United States Patent [19]
Aldovini et al.

[11] Patent Number: 5,861,282
[45] Date of Patent: Jan. 19, 1999

[54] NON-INFECTIOUS HIV PARTICLES AND USES THEREFOR

[75] Inventors: Anna Aldovini; Richard A. Young, both of Winchester, Mass.; Mark B. Feinberg, San Francisco; Didier Trono, Solana Beach, both of Calif.; David Baltimore, New York, N.Y.

[73] Assignee: Whitehead Institute for Biomedical Research, Cambridge, Mass.

[21] Appl. No.: 117,981

[22] Filed: Sep. 7, 1993

Related U.S. Application Data

[63] Continuation of Ser. No. 859,346, Mar. 27, 1992, abandoned, which is a continuation-in-part of Ser. No. 421,817, Oct. 16, 1989, abandoned.

[51] Int. Cl.$^6$ .............................. C12N 5/10; C12N 15/63; C12P 21/02; C07K 14/155
[52] U.S. Cl. .................. 435/69.3; 424/188.1; 424/199.1; 424/208.1; 435/69.1; 435/172.3; 435/235.1; 435/236; 435/320.1; 435/325; 536/23.72
[58] Field of Search ................................. 435/235.1, 236, 435/240.1, 320.1, 69.1, 69.3, 325, 172.3; 514/44; 424/208.1, 205.1, 199.1, 188.1; 536/23.72

[56] References Cited

U.S. PATENT DOCUMENTS

| | | | |
|---|---|---|---|
| 5,017,688 | 5/1991 | Gilbert et al. | 530/326 |
| 5,139,947 | 8/1992 | Kobayashi et al. | 435/172.3 |
| 5,169,763 | 12/1992 | Kieny | 435/69.3 |
| 5,439,809 | 8/1995 | Haynes et al. | 435/69.3 |
| 5,614,404 | 3/1997 | Mazzara et al. | 435/236 |
| 5,665,577 | 9/1997 | Sodroski et al. | 435/172.3 |
| 5,674,720 | 10/1997 | Gorelick et al. | 435/172.3 |

FOREIGN PATENT DOCUMENTS

| | | |
|---|---|---|
| 241239 | 10/1987 | European Pat. Off. . |
| 315459 | 5/1989 | European Pat. Off. . |
| 386882 | 9/1990 | European Pat. Off. . |
| WO 91/06318 | 5/1991 | WIPO . |
| WO 91/07425 | 5/1991 | WIPO . |
| WO 91/19798 | 12/1991 | WIPO . |

OTHER PUBLICATIONS

J. L. Fox, Bio/Technology 12:128 (1994).
Jowett, J.B.M. et al., "Distinct Signals In Human Immunodeficiency Virus Type 1 Pr55 Necessary for RNA Binding and Particle Formation", *J. Gen. Virol.* 73:3079–3086 (1992).
Aldovini, A. and Young, R.A., "Mutations of RNA and Protein Sequences Involved in Human Immunodeficiency Virus Type 1 Packaging Result in Production of Noninfectious Virus", *J. Virol.* 64(5):1920–26 (May 1990).
Gorelick et al., "Noninfectious Human Immunodeficiency Virus Type 1 Mutants Deficient in Genomic RNA", *J. Virol.* 64(7) 3207–3211 (Jul. 1990).
Lever et al., "Identification of a Sequence Required for Efficient Packaging of Human Immunodeficiency Virus Type 1 RNA into Virions", *J. Virol.* 63(9):4085–87 (Sep. 1989).
Gorelick, R.J. et al, "Point Mutants of Moloney Murine Leukemia Virus That Fail to Package Viral RNA: Evidence for Specific RNA Recognition By a Zinc Finger–Like Protein Sequence", *Proc. Nat. Acad. Sci. USA* 85:8420–24 (Nov. 1988).
Meric, C. and Spahr, P–F., "Rous Sarcoma Virus Nucleic Acid–Binding Protein p12 Is Necessary for Viral 70S RNA Dimer Formation and Packaging", *J. Virol.* 60(2):450–459 (Nov. 1986).
Meric, c. et al., "Mutations in Rous Sarcoma Virus Nucleocapsid Protein p12 (NC): Deletions of Cys–His Boxes", *J. Virol.* 62(9) 3328–3333 (Sep. 1988).
Adam, M.A. and Miller, A.D., "Identification of A Signal in a Murine Retrovirus That Is Sufficient for Packaging on Nonretrovirus RNA into Virions", *J. Virol.* 62:3802–3806 (Oct. 1988).
Covey, S.M., "Amino Acid Sequence Homology in gag region of Reverse Transcribing Elements and The Coat Protein Gene of Cauliflower Mosaic Virus", *Nucleic Acids Res.* 14(2):623–633 (1986).
McCune, J.M., et al., "Endoproteolytic Cleavage of gp160 Is Required for the Activation of Human Immunodeficiency Virus", *Cell* 53:55–67 (1988).
Prats, A.C., et al., "Small Finger Protein of Avian and Murine Retroviruses Has Nucleic Acid Annealing Activity and Positions the Replication Primer tRNA onto Genomic RNA", *J. Embo.* 7:1777–1783 (1988).
Trono, D., et al., "HIV–1 Gag Mutants can Dominantly Interfere with the Replication of the Wild–Type Virus", *Cell* 59:113–120 (1989).
Mann, R., et al., "Construction of a Retrovirus Packaging Mutant and Its Use to Produce Helper–Free Defective Retrovirus", *Cell* 33153–159 (1983).
Aldovini and Feinberg, "Transfection of Molecularly Cloned HIV Genomes", in: *Techniques in HIV Research*, Aldovini and Walker (eds.), Stockton Press, New York, 1990, pp.14/ff, 166.
L. Ratner et al. (1985) Nature 313:277–284.
B. F. Haynes (1993) Science 260: 1279–1286.

*Primary Examiner*—Johnny F. Railey, II
*Attorney, Agent, or Firm*—Hamilton, Brook, Smith and Reynolds, P.C.

[57] ABSTRACT

This invention related to constructs comprising mutant HIV genomes having an alteration in a nucleotide sequence which is critical for genomic RNA packaging and non-infectious, immunogenic HIV particles produced by expression of these constructs in mammalian cells. Cell lines which stably produce non-infectious, immunogenic HIV particles are also included. Prophylactic and therapeutic vaccines, diagnostic reagents, and related methods are further described.

26 Claims, 14 Drawing Sheets

FIG. 1A

```
                      splice                                    gag initiation
                      donor                                        codon
pHXB2      GCGACTGGTGAGTACGCCAAAAATTTGACTAGCGGAGGCTAGAAGGAGAGATGGG
pA3HXB     GCGACTGGTGAG----------- 39 bp deletion ----------AGATGGG
pA4HXB     GCGACTGGTGAG--- 21 bp deletion ---CGGAGGCTAGAAGGAGAGATGGG
```

FIG. 1B

```
              5' CysHis box                              3' CysHis box pHXB2       K C FN C GKEG H TARN C RAPRKKG  C WK C GKEG H QMKD C TER
pA14HXB     K Y FN Y GKEG H TARN C RAPRKKG  C WK C GKEG H QMKD C TER
pA15HXB     K C FN C GKEG H TARN C RAPRKKG  Y WK Y GKEG H QMKD C TER
pA14-15HXB  K Y FN Y GKEG H TARN C RAPRKKG  Y WK Y GKEG H QMKD C TER
pΔCH1-2HXB  K -------------- 35 amino acid deletion -------------- TER
```

```
     AlaThrLeuGluGluMetMetThrAlaCysGlnGlyValGlyGly
     CGGCUACACUAGAAGAAAUGAUGACAGCAUGUCAGGGAGUAGGAG
     A                                             G
                            p24
     ProGlyHisLysAlaArgValLeuAlaGluAlaMetSerGlnVal
     GACCCGGCCAUAAGGCAAGAGUUUUGGCUGAAGCAAUGAGCCAAG
                                                1440
            Ser                    p15
     ThrAsnThrAlaThrIleMetMetGlnArgGlyAsnPheArgAsn
     UAACAAAUACAGCUACCAUAAUGAUGCAGAGAGGCAAUUUUAGGA
            U                A
               Ile
     GlnArgLysMetValLysCysPheAsnCysGlyLysGluGlyHis
     ACCAAAGAAAGAUGGUUAAGUGUUUCAAUUGUGGCAAAGAAGGGC
                 U                                 1530
      Ile
     ThrAlaArgAsnCys ArgAla ProArgLysLysGlyCysTrpLys
     ACACAGCCAGAAAUUGCAGGGCCCCUAGGAAAAAGGGCUGUUGGA
          U
     CysGlyLysGluGlyHisGlnMetLysAspCysThrGluArgGln
     AAUGUGGAAAGGAAGGACACCAAAUGAAAGAUUGUACUGAGAGAC
                                                1620
     PhePheArgGluAspLeuAlaPheLeuGlnGlyLysAlaArg
     AlaAsnPheLeuGlyLysIleTrpProSerTyrLysGlyArgPro
     AGGCUAAUUUUUUAGGGAAGAUCUGGCCUUCCUACAAGGGAAGGC
                 └─→pol
     GluPheSerSerGluGlnThrArgAlaAsnSerProThrIle
     GlyAsnPheLeuGlnSerArgProGluProThrAlaProProPhe
     CAGGGAAUUUUCUUCAGAGCAGACCAGAGCCAACAGCCCCACCAU
                              ΔLAV
```

FIG. 2A

```
           SerSerGluGlnThrArgAlaAsnSerProThrArgArgGluLeu
         LeuGlnSerArgProGluProThrAlaProProGluGluSerPhe
       UUCUUCAGAGCAGACCAGAGCCAACAGCCCCACCAGAAGAGAGCU

Leu
         GlnValTrpGlyArgAspAsnAsnSerProSerGluAlaGlyAla
                                Ser
         ArgSerGlyValGluThrThrThrProProGlnLysGlnGluPro
       UCAGGUCUGGGGUAGAGACAACAACUCCCCUCAGAAGCAGGAGC
                                U              1800

AspArgGlnGlyThrValSerPheAsnPheProGlnIleThrLeu
           IleAspLysGluLeuTyrProLeuThrSerLeuArgSerLeuPhe
       CGAUAGACAAGGAACUGUAUCCUUUAACUUCCCUCAGAUCACUCU

TrpGlnArgProLeuValThr IleLys IleGlyGlyGlnLeuLys
           GlyAsnAspProSerSerGln***
       UUGGCAACGACCCCUCGUCACAAUAAAGAUAGGGGGGCAACUAAA
                                               1890
                   gag GluAlaLeuLeuAspThrGlyAlaAspAspThrValLeuGluGlu
       GGAAGCUCUAUUAGAUACAGGAGCAGAUGAUACAGUAUUAGAAGA MetSerLeuProGlyArgTrpLysProLysMetIleGlyGlyIle
       AAUGAGUUUGCCAGGAAGAUGGAAACCAAAAAUGAUAGGGGGAAU
                                               1980
```

FIG. 2B

HT4-6C
HT4(WT-ΔE-dhfr)
HT4(bCA20-ΔE-dhfr)

NON-INFECTIOUS HIV PARTICLES AND USES THEREFOR

RELATED APPLICATION

This application is a continuation of application Ser. No. 07/859,346 filed on Mar. 27, 1992 now abandoned, which is a continuation-in-part of Ser. No. 07/421,817, filed Oct. 16, 1989, now abandoned. The teachings of Ser. No. 07/421,817 are hereby incorporated by reference.

FUNDING

Work described herein was supported by grants from the Public Health Service; the National Institutes of Health; a Burroughs Wellcome Scholar Award; a Fellowship from Suisse de Bourses en Medecine et Biologie; and the Whitehead Institute for Biomedical Research. The U.S. government has certain rights in this invention.

BACKGROUND

Human immunodeficiency virus (HIV) is the causative agent of acquired immune deficiency syndrome (AIDS), which is characterized by immune suppression resulting from selective infection and death of T lymphocytes (Sarin, P., *Ann. Rev. Pharmacol.* 28:411–428 (1988)). Clinical manifestations of the disease include severe immune deficiency, which is generally accompanied by malignancies and opportunistic infections. According to current estimates from the World Health Organization, 1 in 250 people are infected with HIV worldwide.

Due to the devastating effects of the virus and the high mortality rate among HIV-infected individuals, much effort, time and money have been expended in the attempt to develop methods for preventing HIV infection (prophylactic methods) and for treating already infected individuals (therapeutic methods). However, only limited progress has been made to date.

The potential efficacy of a HIV vaccine is suggested by studies in the simian AIDS model system. Vaccines composed of whole, inactivated virions of simian immunodeficiency virus (SIV) were found to confer at least partial protection against challenge with either live virus or cell-associated virus (Langlois, A. J., et al., *Science* 255:292–293 (1992); Le Grand, R., et al., *Nature* 355:684 (1992); Osterhaus, A., and P. De Vries, *ibid., pp.* 684–685; Cranage, M. P., et al., *ibid., pp.* 685–686). It has been observed that "whole, inactivated SIV preparations induce the strongest and most consistent protection thus far experienced in experimental animal studies" (Langlois, 1992 supra).

A major problem in obtaining whole, inactivated HIV vaccines, however, has been presented by the tradeoff between safety and immunogenicity. Killed HIV currently used in human immunotherapy trials is required to be prepared through two independent inactivation protocols, each of which must be adequate to completely inactivate the virus on its own. The physical and chemical inactivation treatments currently used have resulted in some loss of immunogenicity of the vaccine due to partial destruction of the virions. A method which leaves the virion structure intact, yet which renders the virions completely noninfectious, would be a significant improvement in vaccine development.

Besides vaccines, drugs which inhibit various stages of HIV infection of T cells and the HIV life cycle in infected cells have been suggested as another approach in the development of therapies against HIV infection. A considerable amount of information is available on viral entry, reverse transcription of the RNA genome, and expression of viral gene products. In contrast, little is known about packaging of the viral genome, assembly of the virion, and budding of the mature virion from the infected cell. One hindrance to HIV research and drug development is the risk of infection to researchers working with reagents which are contaminated with or derived from live HIV. Thus, a means to produce HIV reagents which are totally noninfectious would relieve some of the cost, in terms of risks to workers, and necessary equipment and facilities, of drug development and HIV research.

SUMMARY OF THE INVENTION

The present invention relates to HIV mutant constructs comprising a mutant HIV genome which has an alteration of a nucleotide sequence critical for packaging the HIV RNA genome, and which, when expressed in mammalian cells, produce non-infectious, immunogenic viral particles. HIV mutant constructs based on HIV-1 and HIV-2 genomes are included. This invention further relates to cell lines, which are stably transfected with the above-mentioned HIV mutant constructs, and which stably produce non-infectious, immunogenic HIV virions. Methods are further included for producing HIV particles which are similar in protein content and morphology to infectious HIV particles, and which are immunogenic, but which are completely non-infectious; these non-infectious mutant HIV particles have been shown to be deficient for the viral genome. The production of these mutant HIV particles, described herein, provides a means to obtain vaccines and diagnostic reagents which are based on immunogenic, but non-infectious virus particles. The production of non-infectious HIV particles further provides an alternative and advantageous method of virus inactivation, referred to as genetic inactivation, for preparation of whole virus vaccines. Such vaccines can be used to induce an anti-HIV response in an individual, either prior to or after infection with HIV, resulting in enhanced resistance by the individual to the virus. Vaccines and reagents which contain non-infectious HIV mutant virions, and methods of prophylactic and therapeutic treatment against HIV are included in the present invention.

In particular, the present invention relates to HIV mutants defective for RNA packaging as a result of nucleotide alterations of the cis-acting RNA packaging site, referred to as the ψ site, and amino acid alterations of the cysteine-rich motifs, alternatively referred to as the CysHis boxes or zinc-knuckle, in the carboxy-terminal region of the Gag precursor.

HIV mutant constructs for preparing non-infectious HIV particles with additional improvements are described. Multiply defective HIV mutants are expected to produce non-infectious HIV virions with a very low probability of reversion to infectivity. These include HIV mutants with multiple defects in both RNA packaging functions, the cleavage site of the gp160 envelope precursor protein, and the primer-binding site. In addition, non-infectious HIV particles with advantageous antigenic properties can be produced. HIV mutants with defective cleavage of the gp160 precursor are expected to have increased retention of the gp120 antigen on the surface of HIV virions. Mutant constructs containing variant envelope genes derived from different HIV strains or isolates can be used to obtain vaccines and diagnostic reagents which are tailored for particular purposes. Variant envelope genes can also be engineered by mutagenesis to increase antigenicity of the vaccines and diagnostic reagents.

BRIEF DESCRIPTION OF THE DRAWINGS

FIGS. 1A–B is a diagram of HIV-1 mutations. A: location and size of deletions affecting the HIV-1 ψ site. (SEQ ID NO:1) B: amino acid changes in the CysHis boxes of HIV-1 Gag produced by various point mutations: (SEQ ID NO:2–4).

FIG. 2 is a partial HIV-1 nucleotide sequence (nucleotides 1351–1980 SEQ ID NO:5) and the deduced amino acid sequence (SEQ ID NO:6) for that partial sequence, showing the location of the mutations in HIV-1 gag described herein. Nucleotide locations are as indicated in Ratner, L., et al., *Nature* 313:277–284 (1985).

Biological Deposits

Figure 3:
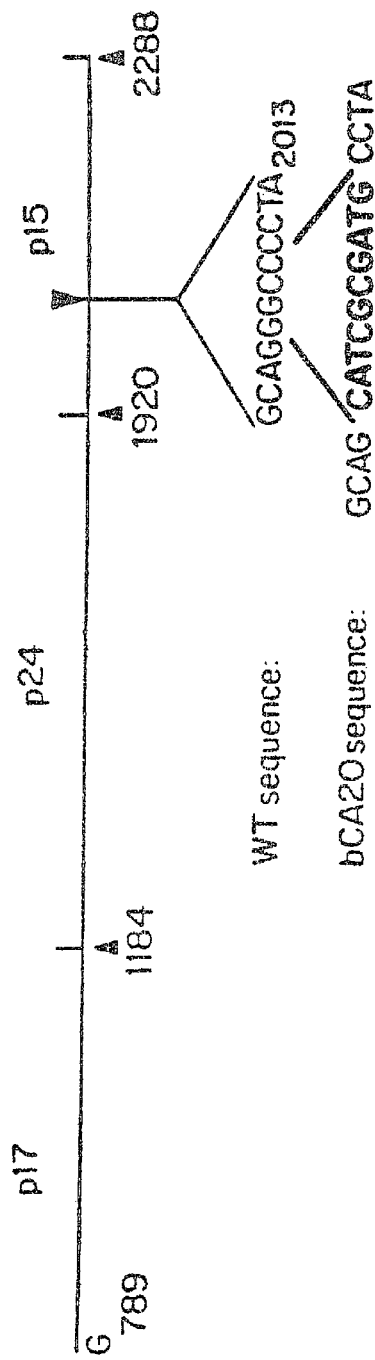
FIG. 3 is a diagram of the gag coding region of HIV-1 with nucleotide numbers indicating the initiation codon, the cleavage sites between p17, p24 and p15, and the gag termination codon. The nucleotide differences between wild type and bCA20 (SEQ ID NO:7) are indicated. Below is shown the amino acid sequence of the two HIV-1 CysHis boxes, and of the intervening sequence, where the bCA20 mutation (SEQ ID NO:8) was introduced.

Three deposits have been made (Oct. 13, 1989 and Oct. 16, 1989) at the American Type Culture Collection, 10801 University Boulevard, Manassas, Va. 20110-2209, in support of the subject application: a HIV-1 Gag CysHis box mutant, designated pA14-15HXB (ATCC Accession #68123); an HIV-1 Gag insertion mutant designated plasmid bCA20-dhfr (ATCC Accession #40682); and a HIV-1 ψ site mutant, designated pA3HXB (ATCC Accession #68122). These deposits have been made under the terms of the Budapest Treaty and, upon grant of a U.S. patent, all restrictions on their availability will be irrevocably removed.

DETAILED DESCRIPTION OF THE INVENTION

This invention is based on work described herein, which demonstrates for the first time, that RNA packaging defects in HIV can result in the production of mutant virions which are similar in morphology and protein content to wild type HIV virions and are immunogenic, but which are completely non-infectious. As described herein, mutant virions are produced by constructing plasmids containing mutated HIV genomes using recombinant DNA techniques and expressing the HIV mutant constructs in mammalian cells. Mutant virions are produced and bud off the cells into the culture medium, where they can be collected. HIV mutant constructs are also used to produce cell lines which stably produce non-infectious HIV particles. Methods for producing the non-infectious HIV particles are described herein which provide improved inactivated vaccines for prophylaxis against and therapeutic treatment of HIV infection, as well as improved methods for obtaining HIV diagnostic reagents. Methods for producing non-infectious HIV particles, HIV mutant constructs and cell lines for producing the particles, and related materials and methods for commercial and medical use are further described below.

HIV-1 RNA Packaging: ψ Site Mutants

The central event of the packaging step is the interaction of the nucleocapsid proteins with the genomic viral RNA to form the core of the virus. This step occurs after transcription and translation of the viral proteins, and before the entire array of interacting viral proteins buds through the cell membranes as mature virions. The packaging step is a very specific and efficient process, during which viral proteins discriminate the genomic RNA from the many spliced viral RNAs and cellular RNAs that exist in the infected cell. For instance, particles containing a spliced mRNA would be defective. Since the retrovirus preferentially packages full length genomic RNA, sequences present exclusively in this RNA but not in spliced viral or cellular RNAs must be involved in the specific RNA-protein interaction that leads to the production of infectious particles.

Viral genomic sequences required for specific packaging have been mapped in several avian and murine retroviruses. These cis-acting sequences, referred to as ψ sites, have been located to a region near the 5' end of the viral genome. The exact boundaries of the ψ sites in the various retroviruses are not known, but sequences between the first splice donor site and the Gag translational start site have been shown to be critical for wild type RNA packaging (Shank, P. R. and M. Linial, *J. Virol.* 36:450–456 (1980); Mann, R. and D. Baltimore, *J. Virol.* 54:401–407 (1985); Linial, M. et al., *Cell* 15:1371–1381 (1978); Koyamat, Harada F. and S. Kawai, *J. Virol.* 51:154–162 (1984); Watanabe, S. and H. M. Temin, *Proc. Natl. Acad. Sci. USA* 79:5980–5990 (1982); Mann, R. and D. Baltimore, *J. Virol.* 54:401–407 (1985)).

Using the defined ψ sites of murine leukemia, spleen necrosis and avian sarcoma viruses as a guide, deletion mutations were constructed in homologous sequences in the HIV-1 genome to investigate whether this region between the first donor splice site and the Gag initiation codon acts as a packaging signal for HIV. Two ψ site mutant constructs were constructed, whose expression resulted in production of non-infectious HIV particles: pA3HXB, which contains a 39 bp deletion of nucleotides 293–331 (inclusive) and pA4HXB, which contains a 21 bp deletion of nucleotides 293–313 (FIG. 2A). The construction of pA3HXB and pA4HXB are described in Example 2.

HIV-1 RNA Packaging: Gag Mutants

In studies of avian and murine retroviruses, there is also evidence that the carboxy-terminus of the Gag precursor can interact with viral genomic RNA. In particular, a cysteine-rich motif, referred to herein as the CysHis box, has been shown to be critical for RNA packaging in Rous sarcoma and Moloney leukemia viruses (Karpel, R. L., et al., *J. Biol. Chem.* 262:4961–4967 (1987); Meric, C. and P.-F. Spahr, *J. Virol.* 60:450–459 (1986); Meric, C., et al., *J. Virol.* 62:3328–3333 (1988); Meric, C. and S. P. Goff, *J. Virol.*

63:1558–1568 (1989); Prats, A. C., et al., *J. EMBO* 7:1777–1783 (1988); Gorelick, R. J., et al., *Proc. Natl. Acad. Sci. USA* 85:8420–8424 (1988)). The CysHis box is present in the carboxy-terminus of all retroviral Gag precursors and has the consensus sequence: $CysX_2CysX_3GlyHisX_4Cys$ (Berg, J., *Science* 232:485–487 (1986)). This motif occurs once in the murine retroviruses, and twice in most other retroviruses studied thus far. Cysteine-rich motifs have been implicated in nucleic acid binding through analogy with the "zinc-finger" motifs present in a wide variety of eukaryotic transcription factors (Evans, R. M. and S. M. Hollenberg, *Cell* 52:1–3 (1988); Berg, 1986 supra). In retroviral nucleocapsid proteins, these sequences may also play a role in protein-protein interactions.

In the HIV infectious cycle, the gag gene is expressed as a protein precursor, $Pr55^{gag}$, which is processed and cleaved into the mature viral proteins, p17, p24, and p15. p15 is believed to be cleaved further into p9 and p7 (Mervis, R. J., et al., *J. Virol.* 62:3993–4002 (1988); Veronese, F. D. M., et al., *J. Virol.* 62:795–801 (1988)). The exceedingly basic character of p15 suggests that it might be associated with the viral RNA (Gelderblom, H. R., et al., *Virology* 156:171–176 (1987)).

The HIV p15 is 123 amino acids long and encoded by the 3' end of the gag gene (FIG. 2). It carries striking similarities with other retroviral nucleocapsid proteins. These similarities include, in the p9 region, two tandem copies, separated by seven amino acids, of a CysHis box (see FIGS. 1B and 3) (Covey, S. N., *Nucleic Acids Res.* 14:623–633 (1986)). To investigate the role of the CysHis box region in packaging of the HIV genome, five HIV-1 mutants were constructed, as shown in FIGS. 1B and 3). Mutant constructs pA14HXB and pA15HXB each encode alteration of a single CysHis box: pA14HXB encodes tyrosine substitutions for $Cys_1$ and $Cys_3$ in the 5' CysHis box (SEQ ID NO:3) and pA15HXB encodes corresponding substitutions in the 3' CysHis box (SEQ ID NO:4). Mutant construct pA14-15HXB encodes tyrosine substitutions for $Cys_1$ and $Cys_3$ in both CysHis boxes. pΔCH1-2HXB encodes a mutant Gag protein with a 35 amino acid deletion of both CysHis boxes and their intervening sequence. Mutant construct bCA20 (FIG. 3) encodes an addition of Ser-Ile-Ala-Met to the intervening peptide sequence immediately after $Cys_{14}$ of the 5' CysHis box (SEQ ID NO:8), thus, changing the distance between the two CysHis boxes. Mutant constructs pA14HXB, pA15HXB, pA14-15HXB, pΔCH1-2HXB and bCA20 were each found to produce non-infectious HIV particles. The construction of the gag mutants are described in the Examples.

Production of HIV-1 Mutant Particles

To observe the effect of the RNA packaging mutations, COS-1 (African Green Monkey kidney) cells were transfected with the above-described HIV mutant constructs for transient expression. The constructs contain the mutated HIV genomes in vectors with an SV40 origin of replication. In COS cells, which express the SV40 large T-antigen, these vectors are replicated in high copy numbers. HIV cannot normally infect COS cells because they lack the CD4 receptor, but once the HIV genome is transfected into these cells, virus is efficiently produced. The expression of viral gene products in these cells can be monitored, and the viral particles released into the supernatant can be collected and characterized.

The virions produced by expression of an HIV construct are referred to herein by the name of the construct but without the preceding "p", for example, A3HXB mutant virions are produced from the pA3HXB mutant construct.

Viral gene expression in the transfected cells was monitored by Northern Blot analysis and by metabolic labelling and immunoprecipitation of viral proteins. Northern blot analysis showed that the patterns of viral RNA from COS cells transfected with the mutant HIV constructs, pA3HXB, pA4HXB, pA14HXB, pA15HXB, and pA14-15HXB, were identical to RNA from cells transfected with a wild type HIV construct, pHXB2gpt. In each case, all three classes of HIV-1 RNA were present: the 9.2 Kb genomic RNA, a 4.3 Kb spliced mRNA encoding the env and vif genes, and the heterogeneous RNAs at about 2 Kb, which includes tat-III, rev, and nef mRNAs. Thus, these HIV-1 mutations do not appear to affect the expression of viral RNAs.

Immunoprecipitation of viral proteins expressed in the transfected COS cells revealed that all of the major structural proteins of HIV-1 are present in cells transfected with either wild type (pHXB2gpt) or mutant (pA3HXB, pA4HXB, pA14HXB, pA15HXB, and pA14-15HXB) HIV-1 constructs. The presence of gp160, gp120, gp41, p24, p17, and p15 in all of the transfected cells indicates that the HIV-1 mutants do not produce major alterations in the synthesis and processing of Gag and envelope precursors.

The amount of HIV virions produced was quantitated by two assays. One was an ELISA that permits assesssment of the level of virus-associated p24 capsid protein. The other was an enzymatic assay that measures the amount of reverse transcriptase activity associated with viral particles. After transfection of COS cells with the HIV mutant constructs, viral particles were pelleted, and analyzed as described above. The results of the p24 ELISA and reverse transcriptase assays are shown in Table 1. The plasmid pHXB2BAMp3 was included as a negative control; it does not produce virus, due to a post-transcriptional defect. These results show that no major differences were observed in the amounts of the two proteins between wild type and mutant particles, indicating that similar levels of wild-type and mutant particles were produced by the transiently transfected cells.

Infectivity of the HIV-1 Mutant Virions

The infectivity of the wild type and packaging mutant virions were assayed on H9 T lymphocytes, which are susceptible to HIV infection. Three different assays were performed during a time course experiment after exposing H9 cells to the supernatants from the transfected cells. The three assays were the following: 1) immunofluorescent staining (IF) with a mouse monoclonal antibody for p24 to measure % of infected cells; 2) core protein p24; and 3) reverse transcriptase (RT) in the supernatant of H9 cells to measure virus released from infected H9 cells. Samples were taken at 3, 6, 9, 12, 16, and 30 days after infection. As shown in Table 2, all the packaging mutants were negative in all three assays up to 30 days after infection. Only wild type virions produced from the pHXB2gpt construct scored positive in these assays. These data indicate that the HIV packaging mutant particles are completely non-infectious.

Biochemical Composition and Morphology of the Mutant Virions

Figure 4:
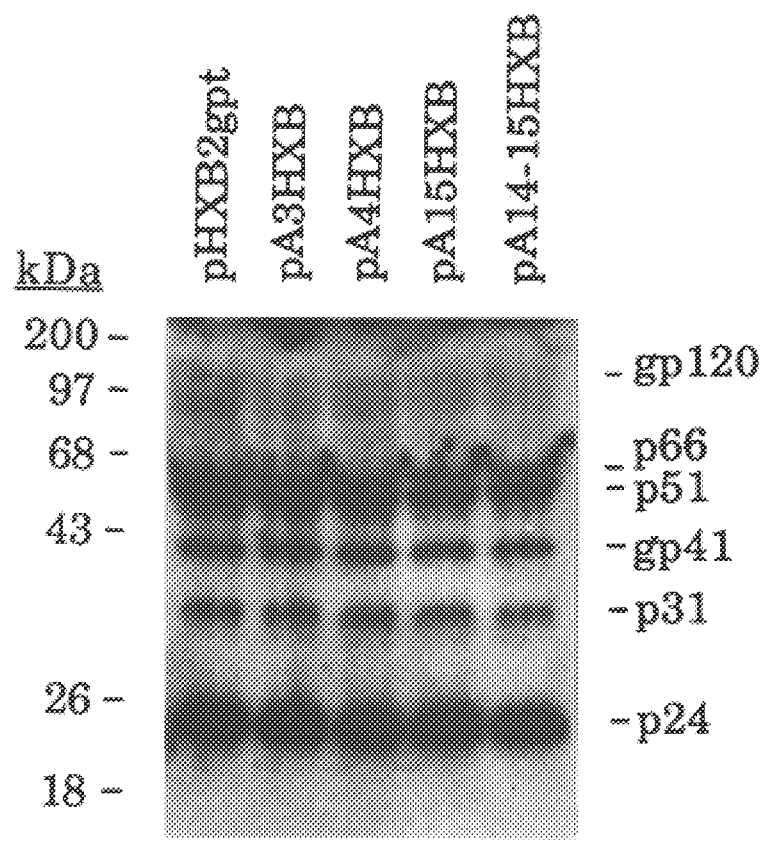
FIG. 4 shows results of Western blot analysis of HIV proteins in HIV-1 mutant particles.
Figure 5:
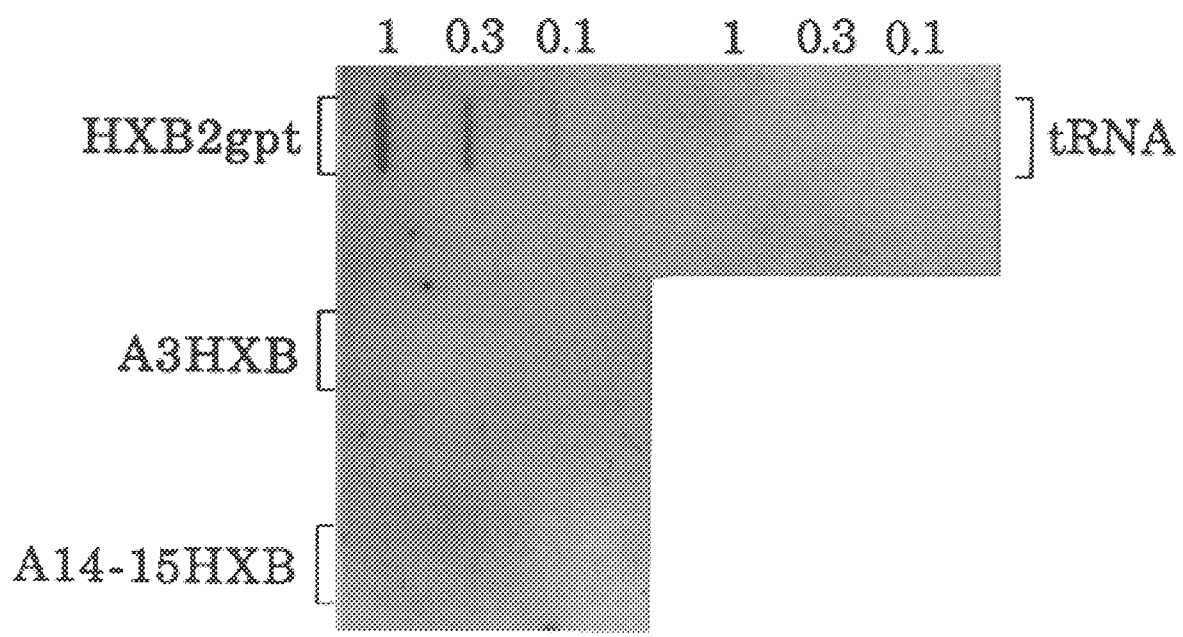
FIG. 5 shows results of Northern blot analysis of HIV RNA in HIV-1 mutant particles.
Figure 6A:
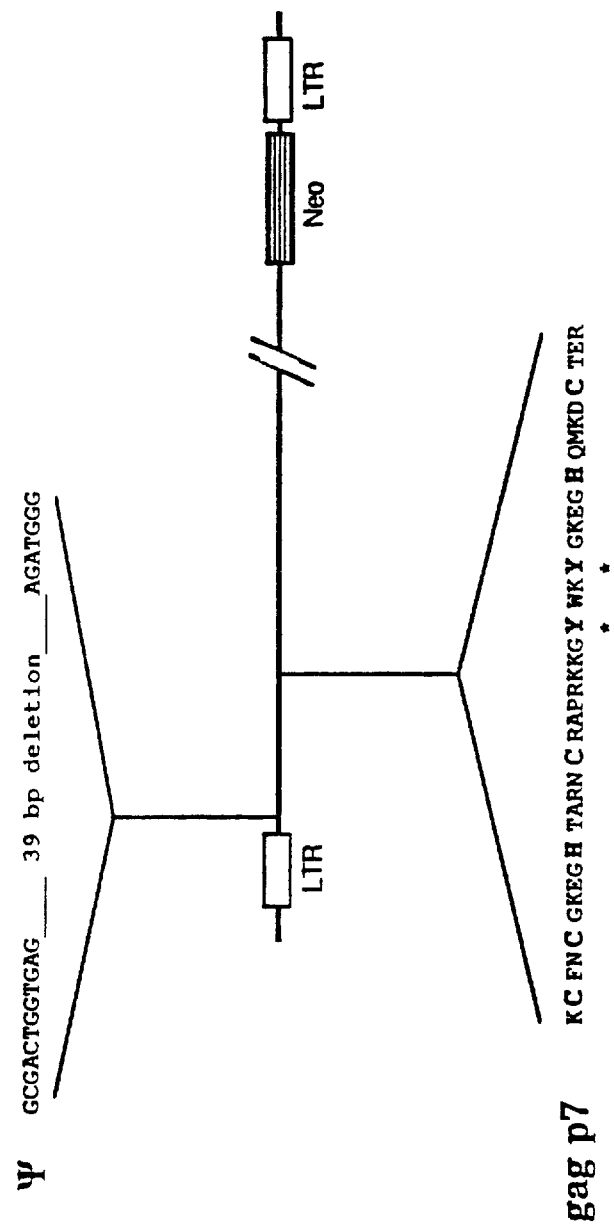
FIGS. 6A–B is a diagram of the HIV-1 mutant constructs: (A) pΔPAC1 and (B) pΔPAC-Hygro.
Figure 6B:
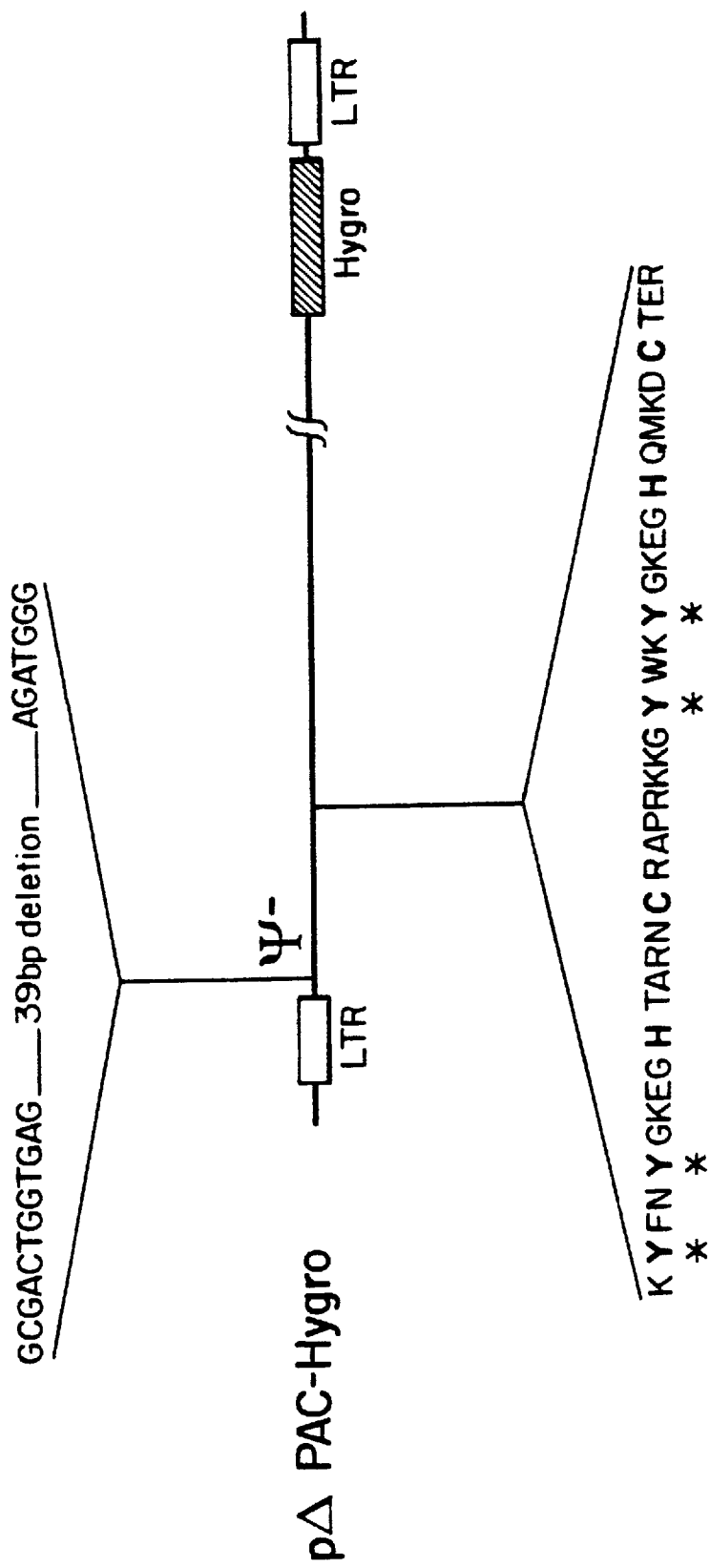
Figure 7:
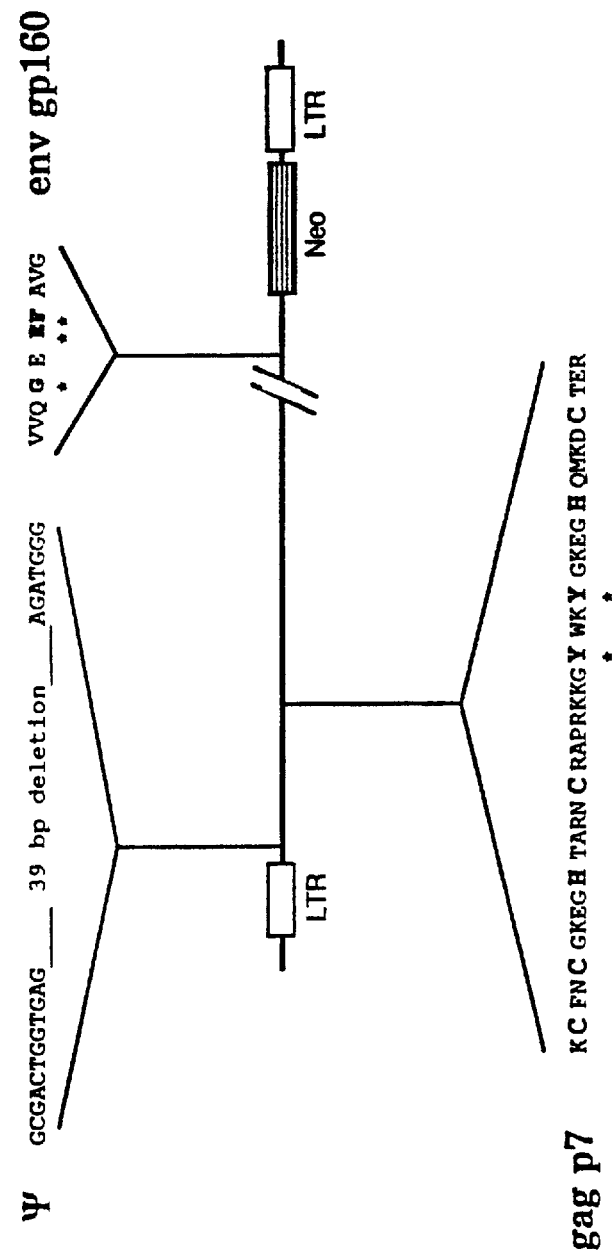
FIG. 7 is a diagram of HIV-1 mutant construct pΔPAC2.
Figure 8:
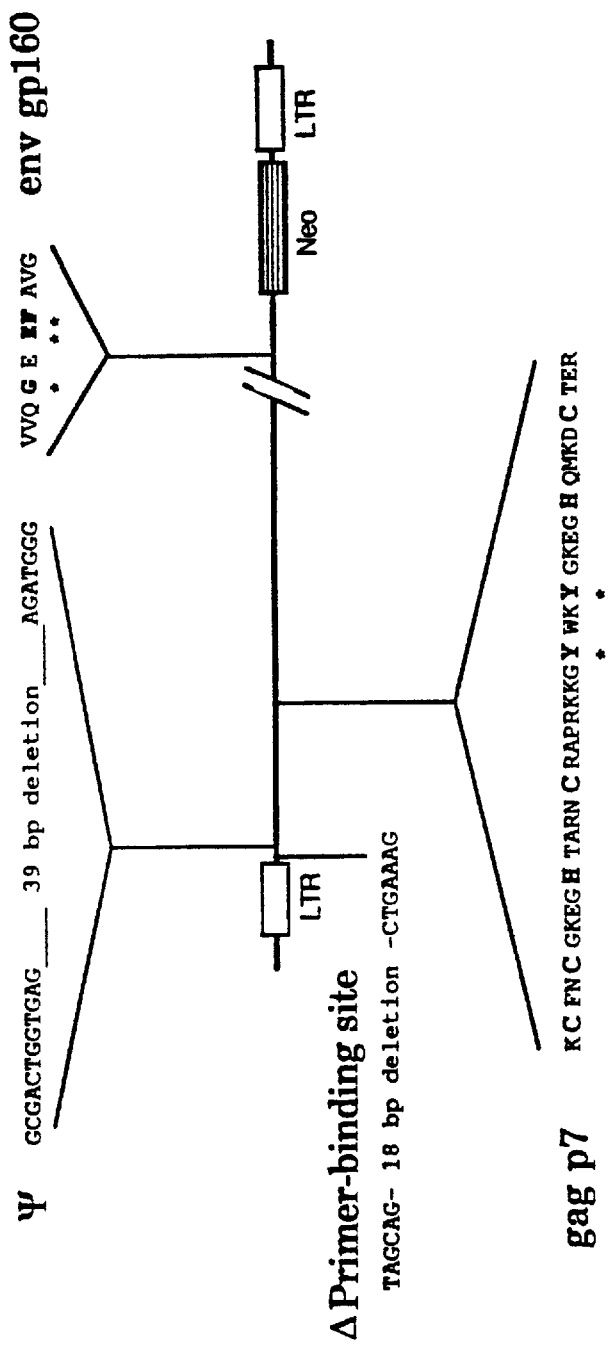
FIG. 8 is a diagram of HIV-1 mutant construct pΔPAC3.

The Northern blot and immunoprecipitation analyses described above indicated no difference in the accumulation of viral RNA and proteins in cells transfected with the mutant and wild type constructs. Western blot analysis was further performed to compare the viral protein composition of the mutant and wild type viral particles; the blot was probed with HIV positive human serum. As shown in FIG. 4, the protein composition of the ψ site mutant virions, A3HXB and A4HXB, and the gag mutant virions, A15HXB and A14-15HXB, was similar to wild type HXB2gpt virions. A14HXB virions, not shown in this figure, gave results similar to A15HXB virions. In each case, viral proteins gp120, p66, p51, gp41, p31 and p24 were observed in about the same relative amounts.

ψ site mutant virions A3HXB and gag mutant virions A14-15HXB were then examined for RNA content by Northern dot blot analysis. As shown in FIG. 5, no genomic RNA was detected in the mutant particles in contrast to wild type HXB2gpt virions. These data indicate that there is at least a 100-fold reduction in the RNA content in both ψ site and CysHis box mutants relative to wild type.

The morphology of mutant HIV particles was examined by electron microscopy. This analysis showed that viral capsids could assemble in the absence of RNA packaging, indicating that mutations in the CysHis box of $p7^{gag}$ can abolish infectivity without affecting virion assembly. Careful scoring of the sections indicated that the majority of the mutant particles were less electron dense than wild type viral particles. This morphology is typical of an immature particle in which viral protein precursors have not been processed. It is possible that the lack of RNA affects the rate of particle maturation or the structural condensation of processed precursors.

Further Improvements of HIV Mutant Constructs

Additional HIV-1 mutant constructs were made for producing non-infectious virions with further improvements. These improvements are expected to possess advantages with regard to safety and antigenicity of mutant virion preparations.

Figure 9:
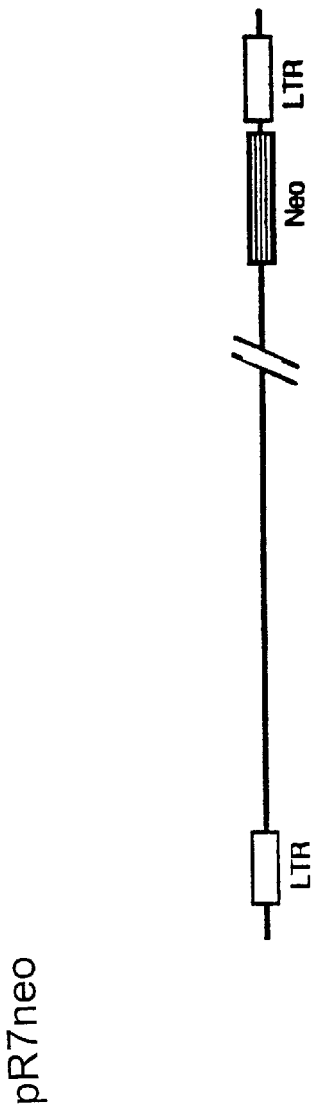
FIG. 9 is a diagram of pR7neo.

RNA packaging mutants with multiple defects are expected to result in non-infectious HIV virions with extremely low probability of reversion to infectivity. Mutant constructs, pΔPAC1 and pΔPAC-Hygro, were made which contain efficacious alterations in both the ψ site and the Gag CysHis region (FIG. 6). The alterations are referred to as efficacious because each alteration alone results in non-infectivity.

Defects in other HIV functions can be added to the packaging defects to decrease even further the risk of reversion. Mutation of the cleavage site of the envelope precursor gp160 has been shown to result in non-infectivity (McCune, J. M., et al., *Cell* 53:55–67 (1988)). A triple defective HIV mutant construct, pΔPAC2, has been made, which contains efficacious alterations of the ψ site, the Gag CysHis box region, and the gp160 cleavage site (SEQ ID NO:9) (FIG. 7). In addition, deletion of the primer binding site, the site near the 5' end of the HIV genome at which a tRNA primer initiates reverse transcription of the viral genome, is expected to abolish infectivity (Prats, A. C., et al., *J. EMBO.* 7:1777–1783 (1988)). A primer binding site deletion is shown in FIG. 8.

Multiply defective HIV mutant constructs can be made containing any combination of the efficacious mutations in RNA packaging and gp160 cleavage and primer binding functions described herein. The ψ site mutation can be the 39 bp deletion of pA3HXB or the 21 bp deletion of pA4HXB (FIG. 1A). The Gag CysHis mutation can result in substitutions in the 5' CysHis box, as in pA-14HXB, the 3' CysHis box, as in pA15HXB, or both CysHis boxes, as in pA14-15HXB; or deletion of one or both CysHis boxes, as in pΔCH1-2HXB (FIG. 1B). Additional mutations of the Env gp160 cleavage site, as in pΔPAC2, and of the primer binding site can be included. An example of a multiply defective HIV construct which contains mutations in all four functions is pΔPAC3 shown in FIG. 8.

Improvements with regard to immunogenic properties of the non-infectious HIV particles can also be made. Mutations of the gp160 cleavage site which block the processing of the gp160 envelope precursor to gp120 and gp41 may reduce the "shedding" of gp120 antigen usually observed during preparation of concentrated HIV virions; the gp41 portion of gp160 is a transmembrane peptide and may serve to anchor more firmly the gp120 antigen to the surface of the virion. This increased retention of gp120 antigen is expected to improve the immunogenic properties of HIV virions produced from gp160 cleavage site mutants. The gp160 cleavage site mutation in pΔPAC3 is defective for both gp160 processing and infectivity, and thus, can be used to produce non-infectious virions with the potentially improved immunogenic properties.

Another means for improving the immunogenic performance of the non-infectious HIV particles in vaccines is to use a strategy in constructing the HIV mutant constructs which will be referred to herein as env replacement technique. The envelope protein is the the surface antigen of HIV and also the most variable protein among HIV isolates. For example, HIV isolates from different geographical locations will contain variable env gene sequences. Many variant env genes have been cloned and sequenced, and are available from the AIDS Research and Reference Reagent Program of the U.S. Department of Health and Human Services, National Institutes of Health (National Institute of Allergy and Infectious Diseases, 6003 Executive Boulevard, Bethesda, Md. 20892). The env replacement technique involves replacing the native env gene in a HIV mutant construct with a variant gene from another HIV strain or isolate in order to tailor the resulting non-infectious HIV particles to a specific use. For example, the mutant particles can be used to vaccinate against HIV strains which are prevalent in a population or against particularly virulent strains. In another example, non-infectious particles used in therapeutic treatment of an infected patient, for instance, to prevent the onset of AIDS symptoms, can be tailored to the particular strain of HIV infecting the patient by isolating virus from the patient, cloning the env gene and replacing the env gene in the mutant construct with the cloned sequence. Alternatively, vaccines can be prepared by combining HIV particles containing a spectrum of various Env proteins for wider protection. The env replacement technique is also useful for obtaining HIV diagnostic reagents which are more specific or more general in detecting various strains of HIV. Variant env genes can also be engineered by mutagenesis of naturally occurring genes in order to produce HIV mutant particles with improved antigenic or immunogenic properties. For example, the Env glycosylation sites could be removed. Env replacement in HIV mutant constructs can be carried out using polymerase chain reaction and other recombinant DNA techniques, as described in the Examples.

Stable Producer Cell Lines

Mammalian cell lines have been generated which stably produce non-infectious HIV virions. The cell lines are produced by stable transfection of cultured cells with HIV mutant constructs containing the packaging and other functional defects described above. Stable transfection procedure includes a selection step for cells which have incorporated the constructs; thus, the transfecting DNA usually contains a selectable marker, such as the neo gene for G418 resistance or hygro for hygromycin resistance. A method of selection for stable transfectants is described herein which is improved over other methods. Previously described methods involved cotransfection of DNA containing the selectable marker with DNA containing the construct of interest, or transfecting with constructs in which the selectable marker is placed under a separate promoter from the coding sequence of interest, usually in the vector. In the selection method described herein, the selectable marker is transcribed from the same promoter as the coding sequence(s) of interest, in this case, the HIV LTR. FIG. 9 shows an HIV construct, pR7neo, in which the nef gene is replaced by a selectable marker (neo). The nef gene does not appear to be essential for the replicative cycle of HIV, since cell lines stably transfected with pR7neo produce wild type, infectious HIV virions. The advantage of this selection method is that expression of the selectable marker is indicative of expression of the coding sequence of interest, and that integration of the construct in the cell genome is such that the transcriptional unit containing the coding sequence and the selectable marker is functional in the cell. This selection method is, thus, more stringent than the former methods, in which expression of the selectable marker is not always indicative of the desired clone.

The construct, pR7neo, is the parent vector from which the HIV mutant constructs used to produce stable producer cell lines were derived. Other HIV mutant constructs for producing stable producer cell lines can be made by engineering combinations of the RNA packaging, Env gp160 cleavage site, and primer binding site defects described above into pR7neo. In addition, selectable markers other than neo can be used to replace the nef gene.

Stable producer cell lines have been generated from COS, HeLa, and H9 cells, as described in the Examples. All three types of cell lines have been found to produce large amounts of HIV particles. In the case of H9-derived cell lines, the amount of particles produced per cell has been observed to exceed production from live virus infection by 40–100 fold. This is a significant additional advantage in terms of production cost.

Other cell lines may also be used to produce non-infectious HIV particles. For example, FDA-approved cell lines may be more convenient for clinical trials.

Immunogenic Properties of Non-infectious HIV Particles

Non-infectious HIV particles produced as described herein were shown to induce antibody responses in mice upon injecting the animals with the HIV mutant particles mixed with an appropriate adjuvant. These results indicate that the non-infectious HIV particles provided by this invention are immunogenic.

Further Commercial and Therapeutic Uses

The present invention provides means for producing HIV mutant particles, which have a similar protein composition and morphology to wild type virons and are immunogenic, but which are completely non-infectious. Furthermore, means are provided for producing HIV mutant particles which are expected to have a very low probability of reversion to infectivity and improved immunogenic properties. The non-infectious HIV particles provided by this invention can be used to obtain improved anti-HIV vaccines and diagnostic reagents. Vaccine compositions and diagnostic reagents related to HIV can now be obtained by the expression in mammalian cells of HIV mutant constructs containing RNA packaging and other mutations, as described herein. These materials can be produced by transient transfection using the constructs or by generating stable producer cell lines by stable transfection with the constructs. Production of non-infectious HIV particles by growing stable producer cell lines is a safer, faster, and more cost-effective method of preparing vaccines and diagnostic reagents than infection with live virus.

The HIV mutant constructs described above are based on HIV-1 genomes. However, constructs based on HIV-2 genomes can also be made using similar methods. Analogous ψ site mutations can be made in the region between the first splice site and the Gag initiation codon. The CysHis box sequences of HIV-2 and HIV-1 are identical; thus, similar tyrosine substitutions of the first two cysteines of either or both CysHis boxes and deletion of the entire CysHis region are expected to result in non-infectious HIV-2 particles. The Env cleavage site of HIV-2 is defined, and can be altered in an analogous manner to the HIV-1 mutation described herein. The HIV-2 primer binding site is also defined, and can be entirely deleted.

Production of non-infectious HIV particles by efficacious mutation of the HIV genome, particularly in sequences critical for RNA packaging, provides a method of inactivating HIV virus for whole virus vaccines. This method of genetic inactivation is less destructive to the virion structure and antigenic surface than heat, chemical cross-linking, and irradiation inactivation methods. Vaccines prepared by a combination of genetic inactivation and one of the other methods are expected to have improved immunogenic properties than virus preparations twice undergoing physical or chemical inactivation. Immunogenicity can be further improved by increased retention of the gp120 surface antigen and by replacement of the env gene with heterologous env genes, as described above.

Vaccines can be prepared which contain inactivated, whole virus particles or antigenic portions of the non-infectious virions. The vaccines can be delivered in an appropriate physiological carrier, such as saline. The carrier can contain an adjuvant, such as BCG (*Mycobacterium bovis* bacillus Calmette-Guerin).

Diagnostic reagents can also be prepared which contain whole or protein derivatives of the non-infectious HIV particles. Protein derivatives can be obtained by disrupting the viral particles, for example, in a buffer containing a detergent. Reagents made from non-infectious HIV particles and their protein derivatives can be used in place of the live virus and live virus derivatives currently used in diagnostic methods. For example, ELISAs or Western blots may be performed to detect anti-HIV antibodies in blood samples. Reagents made from non-infectious HIV particles and protein derivatives would be safer, easier, and less costly to prepare. As described above, stable producer cell lines can produce up to 40–100× the amount of HIV particles per cell than that obtained by infection with live virus.

In addition, stable producer cell lines can be used to produce non-infectious SIV particles for immunotherapy and prophylaxis trials in simian animal models for AIDS. SIV mutant constructs with RNA packaging, Env gp160 cleavage and primer binding site mutations corresponding to the HIV mutations described herein have been made in parallel for this purpose.

In addition, stable producer cell lines provide a convenient and safe in vitro model system to study post-infection events in the HIV life cycle. Increased knowledge of mechanisms by which HIV reproduce in mammalian cells may lead to novel therapies for preventing or controlling HIV infection.

Furthermore, stable producer cell lines provide a safe and convenient method for identifying drugs which inhibit production of HIV particles from infected cells. For instance, the drugs may disrupt virion assembly or budding. HIV inhibitory drugs could be used to reduce the severity of disease in an infected individual.

EXAMPLES

The present invention will now be illustrated by the following examples, which are not intended to be limiting in any way.

Cell Lines and Viruses

The simian virus 40-transformed African green monkey cell line, COS-1, has been described (Gluzman, Y., *Cell* 23:175–182 (1981)). The cell line was obtained from G. Khoury (National Institutes of Health) and is available from the American Type Culture Collection (Rockville, Md.). COS-1 was maintained in Dulbecco modified Eagle medium supplemented with 10% fetal bovine serum. The H9 and H9 IIIB T-lymphoid cell lines were maintained as described previously (Popovic, M., et al., *Science* 224:497–500 (1984) ). Viral infections and reverse transcriptase assays were carried out as described previously after filtration of culture supernatants through a 0.45-$\mu$m-pore-size filter (Millipore Corp., Bedford, Mass.) (Popovic, et al., 1984 supra; Daniel, M. D., et al., *Science* 228:1201–1204 (1985)).

Mutagenesis of the HIV-1 Genome and Plasmid Construction

The parent DNA used for these studies is the biologically active clone, pHXB2gtp (Fisher, A. G., et al., *Nature* (London) 316:262–265 (1985)). The SacI-SalI 5.3 kilobase pair (Kb) fragment (nucleotides 39 to 5366) was cloned in M13mp18, and oligo-mediated site-directed mutagenesis was performed on the single stranded DNA according to the protocol of Kunkel, T. A., et al. (*Methods in Enzymology* 154:367–382 (1987)). Nucleotide positions in the HIV-1 genome are numbered as previously described (Ratner, L., et al., *Nature* 313:277–284 (1985)).

Deletions and substitutions of the HIV-1 genome were made by site-directed mutagenesis using synthetic primers having appropriate segments of the genomic sequence. For example, the following oligomers were used to obtain the ψ site mutations:

A3: TGACGCTCTCGCACCCATCTCTCACCAGTCGCCGCCCCTC (SEQ ID NO:10), for deleting nucleotides 293 to 331; and A4: CTCTCTCCTTCTAGCCTCCGCTCACCAGTCGCCGCCCCTC (SEQ ID NO:11), for deleting nucleotides 293 to 313; and the gag mutations:

A14: TGCCCTTCTTTGCCATAATTGAAATACTTAACAATCTTTC (SEQ ID NO:12), for changing guanines (G) at positions 1508 and 1517 to adenines (A); and A15: TGTCCTTCCTTTCGATATTTCCAATAGCCCTTTTTCCTAG (SEQ ID NO:13), for changing G at positions 1571 and 1580 to A. The RNA packaging mutations in pA3HXB, pA4HXB, pA14HXB, pA15HXB, pA14-15HXB were made using these primers. Deletion of the entire CysHis box coding region for constructing pΔCH1-2HXB and of the 18 bp primer binding site, as illustrated in FIG. 8, was performed similarly using appropriate primers.

The introduction of the mutations was verified by sequencing different M13mp18 recombinant DNAs using two specific oligomers: A5: CCATCGATCTAATTCTC (SEQ ID NO:14) and A16: GGCCAGATCTTCCCTAA (SEQ ID NO:15) (Ausubel, F. M., et al., *Current Protocol in Molecular Biology,* Green Publishing Associates and Wiley Interscience (1987)).

A BsshII/SalI 1.9 Kb DNA fragment from the mutated M13mp18 recombinant clones was used to transfer all the different mutations to the wild-type plasmid pHXB2gpt. The entire region that had been transferred from the M13mp18 plasmids was sequenced using double stranded DNA sequencing methods (Ausubel, F. M. et al., 1987 supra) to confirm the presence of the desired mutations and the absence of any other alterations. All DNA manipulations were according to standard procedures.

Mutation of the Env gp160 cleavage site, as illustrated in FIG. 8, has been described in McCune, J. M., et al., which is hereby incorporated by reference (*Cell* 53:55–67 (1986)).

Replacement of the nef gene with a selectable marker has been described in Trono, D., et al., which is hereby incorporated by reference (*Cell* 59:113–120 (1989)).

Replacement of the native env gene with a variant gene is carried out by polymerase chain reaction using DNA containing the variant HIV genomic sequence as templates and primers containing restriction sites appropriate for cloning the amplified DNA into the HIV construct. Restriction sites can be engineered into the HIV genome by site-directed mutagenesis, if necessary. DNA containing HIV genomic sequences of various HIV strains and isolates can be obtained from the National Institutes of Health repository, or can be obtained from HIV-infected patients by isolating the virus and cloning the viral genome. In addition, mutated env genes, including genes encoding defective glycosylation sites, can be engineered by site-directed mutagenesis.

Transfection of Mammalian Cells with HIV Constructs

COS-1 cells were seeded at a density of $10^6$ per 100 mm plate, 24 hours prior to transfection, in DME medium supplemented with 10% fetal calf serum and incubated at 37° C. in 5% $CO_2$. Transfection was carried out using 10 $\mu$g of plasmid DNA/plate as described (Chen, C. and H. Okoyama, *Mol. Cell. Biol.* 7:2745–2752 (1987)).

When viral particles were destined for RNA analysis, transfections in COS cells were performed according to the method of Selden et al. (Selden, R. F., et al., *Mol. Cell. Biol.* 6:3173–3179 (1986)) to avoid the heavy DNA contamination of samples that was observed when calcium phosphate transformation was performed.

Stable producer cell lines were generated by selecting for stable transfectants possessing antibiotic resistance conferred by the selectable marker in the construct. Transfection was carried out by either the $CaPO_4$ or electroporation methods. Stable transfectants were selected using G418 or hygromycin (Gibco) at appropriate concentrations for the cell line, as determined by killing assays. In general, a concentration was used which gave 80% cell death in a week. The resistant clones were collected and pooled, and grown in the presence of the antibiotic. Over time, the pooled stable producer cells increased their HIV particle production as the cell population purified under continued selective pressure. Alternatively, resistant clones could be purified through several rounds of replating rather than pooled. Individual clones could be tested for maximum HIV production.

Analysis of Viral RNA

For analysis of RNA in transfected cells: RNA was extracted from COS-1 cells 48 hours after transfection, using the hot phenol method described by Queen and Baltimore (Queen, C. and D. Baltimore, *Cell* 33:741–748 (1983)). For Northern blot analysis, 10 μg of DNase I-treated total cellular RNA was used per lane. RNA from mock transfected COS-1 cells was used as a negative control and 5 μg of RNA from H9 cells, chronically infected with HXB2 virus, was used as a positive control The HIV-1 specific probe was a $^{32}$P-labelled full length viral DNA.

For analysis of RNA in viral particles: RNA was extracted from supernatants containing equal amounts of p24 in the presence of equal amounts of added tRNA; the tRNA was used to monitor the final recovery of RNA. RNA samples were resuspended in water at identical concentrations of tRNA (1 μg/ml) and 1, 0.3 and 0.1 equivalents of RNA were loaded on nitrocellulose, where one equivalent represents the amount of RNA obtained from COS-1 supernatants containing 18 ng of p24. RNA Slot Blot analysis was performed as previously described (Ausubel et al., 1987 supra). A 3.8 Kb ClaI/EcoRI gag-pol fragment from pHXB2gpt was labelled with $^{32}$p by random priming and used as probe for the Slot Blot.

Analysis of Viral Proteins

For analysis of proteins in transfected cells: COS-1 cells ($4\times10^6$) transfected 48 hours earlier with 10 μg of each plasmid were labelled for 4 hours with 500 μCi of $^{35}$S methionine. As a negative control, cells were transfected with the plasmid pHXB2Bamp3, which does not produce virus due to a post-transcriptional defect (Feinberg, M. B., et al., *Cell* 46:807 (1986)). Cell lysates were prepared and immunoprecipitations were performed as described (Veronese, F. D., et al., *Cell* 46:807 (1986)), using HIV-1 positive human serum which had demonstrated reactivity with all known viral structural proteins (Feinberg et al., 1986 supra)). Immunoprecipitated proteins were resolved using a 10% SDS-polyacrylamide gel (Laemmli, U. K., *Nature* 227:680 (1970)).

For analysis of proteins in HIV particles: virus was pelleted by centrifugation for three hours at 27,000 rpm in a SW27 rotor. The pellet was resuspended in dissociation buffer (0.01M Tris-HCL pH 7.3, 0.2% Triton X-100, 0.001M EDTA, 0.005M dithiothreitol (DTT), 0.006M KCL), if reverse transcriptase activity was to be measured, or in 0.2% Triton and Laemli buffer if protein analysis was to be performed. Western blot analysis and radio-immunoprecipitations (RIP) followed the procedure of Veronese et al. (Veronese, F. D., et al., *Proc. Natl. Acad. Sci. USA* 82:5199–5202 (1985)). p24 analysis on tissue culture supernatants or on pelleted virus was performed.

Amounts of p24 gag protein (ng/ml) in the supernatant of each mutant were determined 48 hours after transfection. Each transfection was overlayed with 10 ml of medium. A DuPont p24 ELISA kit was used and three different dilutions of each supernatant were analyzed. RT activity was measured after concentrating 3 ml of COS-1 supernatant from transfections of each mutant by centrifugation for three hours at 27,000 rpm. Numbers refer to 1 ml of supernatant and are the mean of three experiments. Analysis of protein content of wild-type and mutant particles by radio-immunoprecipitation was also done.

Infectivity Assays

H9 cells were infected by filtered (0.45 μm, Millipore) supernatants from COS-1 cells that had been transfected 48 hours. Immunofluorescence assays were performed with murine monoclonal antibody specific for the p24$^{gag}$ protein (Veronese, F. D., et al., *Proc. Natl. Acad. Sci. USA* 82:5199–5202 (1985)) and the h9-HIV IIIB cell line as a positive control. p24 assays were performed with a p24 ELISA (DuPont Co.). Reverse transcriptase assays were carried out after filtration of culture supernatants (Daniel, M. D., et al., *Science* 228:1201–1204 (1985)).

Construction and Analysis of bCA20

To address the role of HIV-1 p15$^{gag}$, a mutation was introduced into plasmid W13 (Kim, et al., *J. Virol.,* 63: 3708–3713(1989) ), which contains an infectious copy of the HIV-HXB2-D proviral DNA. (Shaw, et al., *Science* 226:1165–1171 1984)) W13 was modified by inserting an 8-nucleotide long ClaI linker in a unique ApaI site present at position 1549, and then blunting this ClaI site with Klenow to rectify the Gag reading frame. The mutated construct thereby obtained is called bCA20-W13. The mutation results in the replacement of the two residues which immediately follow the first Cys His box, arginine-alanine, by a stretch of four amino acids, serine-isoleucine-alanine-methionine (FIG. 3). Therefore, both the amino acid sequence and length of the intervening sequence between the two Cys-His boxes is altered.

To analyze the phenotypic consequences of the mutation, COS cells were transfected with bCA20 and generation of viral particles was scored by measuring the amount of p24 antigen as well as the reverse transcriptase activity released in the supernatant (Table 3).

TABLE 3 p24 Antigen[a] and Reverse Transcriptase
(RT) Activity[b] in the Supernatant of Transfected COS
Cells and HT4 (ΔE-dhfr) Cell Lines

|  | p24 antigen (ng/ml) | RT activity (cpm/ml) |
|---|---|---|
| COS Transfectants |  |  |
| W13 (WT) | 120 | 23,000 |
| bCA20-W13 | 50 | 7,300 |
| HT4 Cell Lines |  |  |
| HT4 (WT-ΔE-dhfr) | 400 | 75,000 |
| HT4 (bCA20-ΔE-dhfr) | 180 | 20,000 |

[a]p24 antigen was measured using an Elisa assay system (Dupont-NEN, Inc., Billerica, MA)
[b]RT activity was determined as described (Kim et al., J. Virol., 63:3708-3713 (1989))

bCA20-induced p24 and reverse transcriptase activities were approximately 40% and 30% of wild-type, respectively. This indicated that the mutation present in bCA20 only mildly interfered with the release of viral particles. The COS cell supernatant was then used to infect H9 cells, which were followed by an indirect immunofluorescence assay (Ho, D. D., et al, *Science* 226:451–453 1984)), using serum from an HIV-infected individual as detector antibody. After three weeks, no positive cells were seen. This showed that the particles generated following transfection were non-infectious. Therefore, it could be concluded that the bCA20 mutation was lethal for viral replication.

Figure 10:
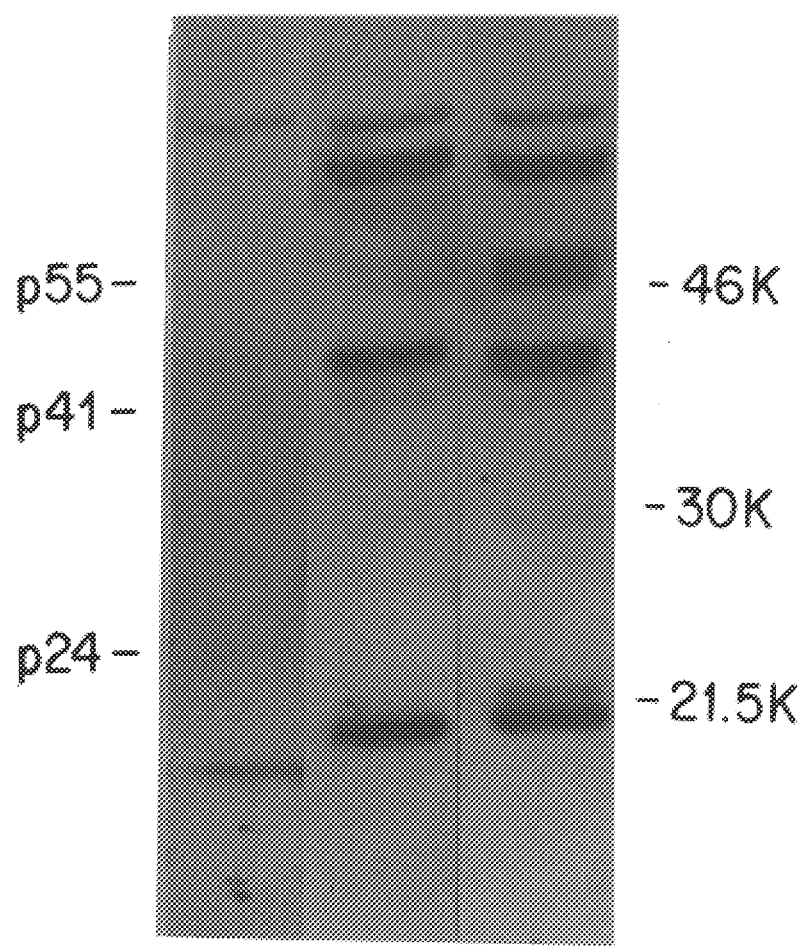
FIG. 10 shows the result of immunoblot analysis of cytoplasmic extracts from HT4(Δ-dhfr) cells.

To further study the consequences of the p15$^{gag}$ mutation contained in bCA20, a cell line which constitutively expresses an Env$^-$ version of this mutant was generated. Expression of the HIV gag gene products is sufficient to generate viral particles in the absence of Env. Such cell lines are made as follows: Briefly, HT4-6C cells (a HeLa cell line expressing the CD4 molecule at its surface) were transfected with construct bCA20-ΔE-dhfr, a modified version of bCA20-W13 which contains a translational frameshift in the env gene and the mutant dihydrofolate-reductase gene in place of the nef reading frame. The HT4-6C cells were a gift from B. Chesebro (Chesebro, B. and Wehrly, K., *J. Virol.* 62:3779–3788 (1988)). Cells were selected for resistance to methotrexate, cloned, and analyzed by polymerase chain reaction to check for the presence of the viral integrant (not shown). Indirect immuno-fluorescence, using serum of an HIV-infected individual as detector antibody, was also performed. The immunofluorescence seen in HT4(bCA20-ΔE-dhfr) was similar to that observed in HT4(WT-ΔE-dhfr), which expresses a wild-type gag sequence (not shown). p24 antigen and reverse transcriptase activity were also measured in the supernatants of these cell lines; the ratio of activity of bCA20 to wild-type was grossly similar to those observed with the transient transfection of the corresponding W13 viral constructs (Table 3). In addition, Western Blot analysis of cytoplasmic proteins was performed as described previously by Trono and co-workers (Trono, C., et al., *Cell,* Oct. 6, 1989), using an anti-p24 monoclonal antibody (a gift from F. Veronese) as detector antibody. HT4(bCA20-ΔE-dhfr) and HT4(WT-ΔE-dhfr) gave similar patterns (FIG. 10). Therefore, it could be concluded that the mutation present in bCA20 did not affect the synthesis, the cleavage or the stability of the Gag precursor.

Figure 11:
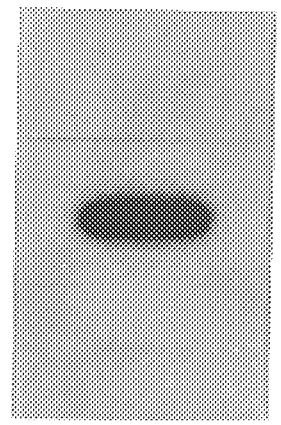
FIG. 11 shows the results of Northern slot blot analysis of viral RNA in the supernatant from HT4(ΔE-dhfr) cells.
Figure 12A:
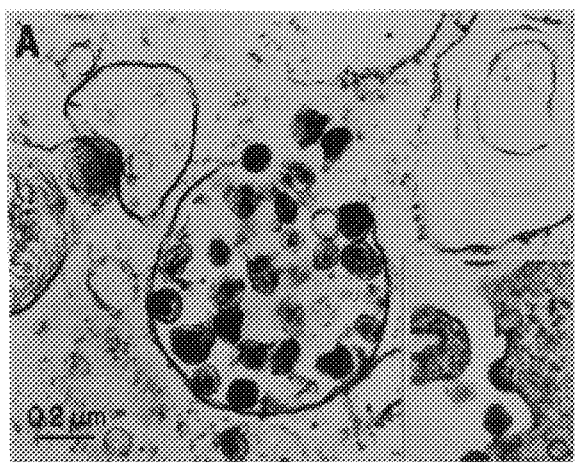
FIGS. 12A–D shows results of examination of HT4(R7-dhfr), HT4(WT-ΔE-dhfr) and HT4(bCA20-Δdhfr) by electron microscopy. Panel A: HT4(R7-dhfr); Panel B: HT4 (WT-ΔE-dhfr); Panel C: HT4(bCA20-ΔE-dhfr). Pictures were taken at a magnification of x38,500 for panels A, B, and C, and x4,500 for the negative control in panel D.
Figure 12B:
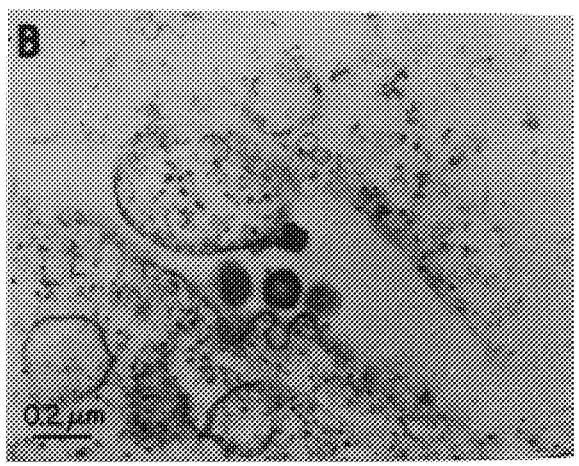
Figure 12C:
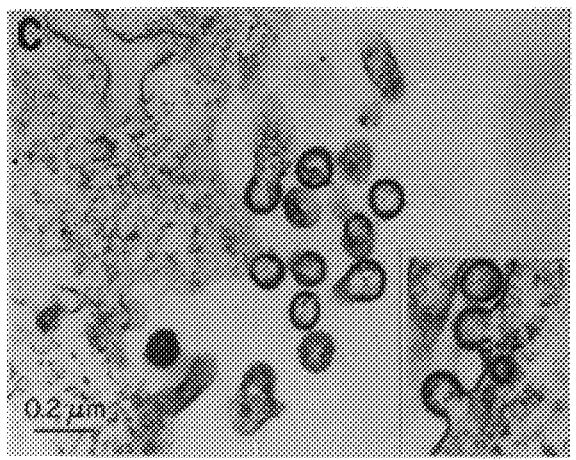
Figure 12D:
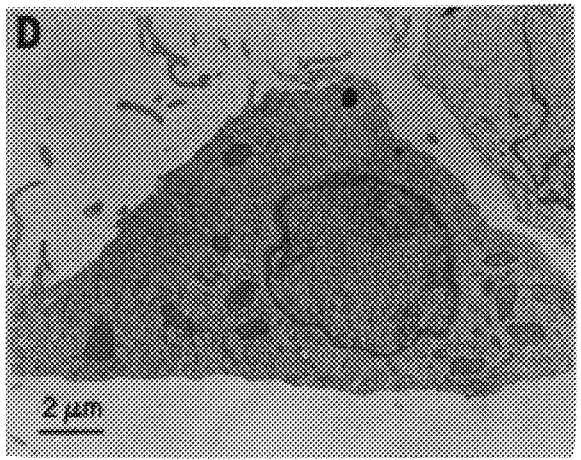

To ask whether the mutation contained in bCA20 had deleterious consequences on the packaging of the viral RNA, a slot-blot analysis of the supernatant from HT4(WT-ΔE-dhfr) and HT4(bCA20-ΔE-dhfr) cells was performed. For this, 700 μl of culture medium was mixed with 35 μl of 10 mg/ml proteinase K (Boehringer, Mannheim), 7 μl of culture medium was mixed with 35 μl of 10 mg/ml tRNA, 3.5 μl 0.5M EDTA, 17.5 μl 20% SDS, incubated at 37° C. for 45 minutes, phenol-extracted and ethanol precipitated in 0.4M NaCl. The RNA was resuspended in 20 μl mM EDTA, denatured in 50% formamide-17% formaldehyde, heated to 50° C. for 20 minutes, mixed with 120 μl 15xSSC, and bound to nitrocellulose by aspiration through a slot blot apparatus. Hybridization was then performed as previously described (Trono, D., et al., *J. Virol.* 62:2291–2299 (1988)), using a [$^{32}$P] probe generated with T7 polymerase which is complementary to nucleotides 8475 to 8900 of the HIV-1 genome. After hybridization, the filter was washed in 0.2xSSC three times at 68° C. and exposed to X-ray film. Results showed that the amount of viral RNA present in the supernatant from HT4(bCA20-ΔE-dhfr) was dramatically reduced, compared to the control cell line, HT4(WT-ΔE-dhfr) (FIG. 11). Therefore, it was concluded that the bCA20 mutation specifically inhibited the packaging of the viral genomic RNA into particles.

Both cell lines were also examined by electron microscopy, to see if the defect in viral RNA packaging correlated with morphological differences (FIG. 12). The morphology of the virus particles observed in HT4(WT-ΔE-dhfr) was very similar to that observed in HT4(R7-dhfr), a cell line infected with an Env$^+$, replication competent version of the same virus: cell-released, "mature" particles contained a condensed core surrounded by the viral lipid bilayer (FIG. 12, Panel A and Panel B). By contrast, in particles released from HT4(bCA20-ΔE-dhfr), two dramatic differences were noted. First, the diameter of the particles was approximately 50% larger than observed in the controls; second, the electron-dense region was tightly apposed to the membrane, but the center of the particles was strikingly electron-luscent (FIG. 12, Panel C). Still, approximately 1% of the bCA20 particles had a morphology close to that of wild-type, probably because of some leakage in the bCA20 phenotype, as already suggested by the RNA hybridization study on the cell supernatant. These electron microscopy findings indicate that the inability to package the viral RNA IN bCA20 particles is accompanied by an increased diameter and an absence of "collapse" of the inner components of the virion, which normally reflects the final steps of maturation. It remains to be determined whether this block of maturation is primarily due to the absence of viral RNA in the particle, or is a direct consequence of the aberrant p15$^{gag}$ protein. Interestingly, the HIV-1 virions produced by cells transfected with the bCA20 p15$^{gag}$ variant provirus bear a notable resemblance to the virus-like particles released from *Spodoptera frugiperda* insect cells infected with a recombinant baculovirus expression vector encoding the p57$^{gag}$ precursor of the simian immunodeficiency virus, SIV$_{mac}$ (Delchambre, M., et al., *EMBO J.* 8:2653–2660 (1989)). Comparison of the morphologic features of the RNA-minus particles produced in these diverse setting suggests that the viral RNA itself may play an important role in the structural organization and maturation of the mature retroviral virion.

In conclusion, as a result of this assessment of the phenotype of an in vitro-engineered HIV-1 variant, bCA20, which contains a mutation between the two Cys His boxes of the p15$^{gag}$ protein, it has been demonstrated that this domain is critical to the packaging of the genomic RNA into the virus particle. In addition, it has been shown that the RNA-deficient phenotype generated by the p15$^{gag}$ lesion is associated with striking morphological anomalies, as shown by electron microscopy. Importantly, results indicate that it is possible to generate HIV particles that do not contain the viral genome. This is of primary relevance for the development of a vaccine strategy based on intact, fully immunogenic, but non-infectious virus particles.

Equivalents

Those skilled in the art will recognize, or be able to ascertain, using no more than routine experimentation, many equivalents to the specific embodiments of the invention described specifically herein. Such equivalents are intended to be encompassed in the scope of the following claims.

TABLE 1 p24 Content and Reverse Transcriptase Activity

| Plasmid Construct | Virus Associated p24 (ng/ml) | Reverse Transcriptase Activity ($^{32}$P dGTP cpm/ml/min) |
| --- | --- | --- |
| pHXB2gpt | 1.90 | 5060 |
| pA3HXB | 1.70 | 3133 |
| pA4HXB | 1.60 | 2718 |
| pA15HXB | 1.75 | 3436 |
| pA14-15HXB | 1.65 | 2949 |
| pHXB2Bamp3 | 0.00 | 740 |

TABLE 2

| Plasmid construct | day 3 | 6 | 9 | 12 | 16 | 30 | |
|---|---|---|---|---|---|---|---|
| pHXB2gpt | 0.5 | 5 | 30 | 65 | 90 | 90 | IF (% of positive control) |
| pA3HXB, pA4HXB pA15HXB, pA14HXB | | | negative | | | | |
| pHXB2gpt | >20 | >20 | >20 | >20 | >20 | >20 | p24 (ng/ml) |
| pA3HXB, pA4HXB pA15HXB, pA14HXB | | | negative | | | | |
| pHXB2gpt | nd | 32.0 | 91.4 | 156.6 | 56.7 | 56.6 | reverse transcriptase ($^{32}$P dGTP cpm/ml/min × $10^3$) |
| pA3HXB, pA4HXB pA15HXB, pA14HXB | | | negative | | | | |

---

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 57 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

GCGACTGGTG AGTACGCCAA AAATTTTGAC TAGCGGAGGC TAGAAGGAGA GAGATGG    57

( 2 ) INFORMATION FOR SEQ ID NO:2:

( i ) SEQUENCE CHARACTERISTICS:
        ( A ) LENGTH: 39 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Lys  Tyr  Phe  Asn  Tyr  Gly  Lys  Glu  Gly  His  Thr  Ala  Arg  Asn  Cys  Arg
1                  5                        10                         15
Ala  Pro  Arg  Lys  Lys  Gly  Cys  Trp  Lys  Cys  Gly  Lys  Glu  Gly  His  Gln
              20                       25                         30
Met  Lys  Asp  Cys  Thr  Glu  Arg
              35
```

( 2 ) INFORMATION FOR SEQ ID NO:3:

( i ) SEQUENCE CHARACTERISTICS:
        ( A ) LENGTH: 39 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Lys  Cys  Phe  Asn  Cys  Cys  Lys  Glu  Gly  His  Thr  Ala  Arg  Asn  Cys  Arg
1                  5                        10                         15
```

```
      Ala  Pro  Arg  Lys  Lys  Gly  Tyr  Trp  Lys  Tyr  Gly  Lys  Glu  Gly  His  Gln
                 20                      25                      30

Met  Lys  Asp  Cys  Thr  Glu  Arg
                 35
```

( 2 ) INFORMATION FOR SEQ ID NO:4:

( i ) SEQUENCE CHARACTERISTICS:
        ( A ) LENGTH: 39 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
      Lys  Tyr  Gly  Asn  Tyr  Gly  Lys  Glu  Gly  His  Thr  Ala  Arg  Asn  Cys  Arg
        1                 5                      10                      15

Ala  Pro  Arg  Lys  Lys  Gly  Tyr  Trp  Lys  Tyr  Cys  Lys  Glu  Gly  His  Gln
                 20                      25                      30

Met  Lys  Asp  Cys  Thr  Glu  Arg
                 35
```

( 2 ) INFORMATION FOR SEQ ID NO:5:

( i ) SEQUENCE CHARACTERISTICS:
        ( A ) LENGTH: 630 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 3..518
        ( D ) OTHER INFORMATION: /product="Gag"

( x i ) SEQUENCE DESCRIPTION: SEQ ID NO:5:

```
CG  GCU  ACA  CUA  GAA  GAA  AUG  AUG  ACA  GCA  UGU  CAG  GGA  GUA  GGA  GGA          47
    Ala  Thr  Leu  Glu  Glu  Met  Met  Thr  Ala  Cys  Gln  Gly  Val  Gly  Gly
      1                 5                      10                      15

CCC  GGC  CAU  AAG  GCA  AGA  GUU  UUG  GCU  GAA  GCA  AUG  AGC  CAA  GUA  ACA          95
Pro  Gly  His  Lys  Ala  Arg  Val  Leu  Ala  Glu  Ala  Met  Ser  Gln  Val  Thr
                 20                      25                      30

AAU  ACA  GCU  ACC  AUA  AUG  AUG  CAG  AGA  GGC  AAU  UUU  AGG  AAC  CAA  AGA         143
Asn  Thr  Ala  Thr  Ile  Met  Met  Gln  Arg  Gly  Asn  Phe  Arg  Asn  Gln  Arg
                 35                      40                      45

AAG  AUG  GUU  AAG  UGU  UUC  AAU  UGU  GGC  AAA  GAA  GGG  CAC  ACA  GCC  AGA         191
Lys  Met  Val  Lys  Cys  Phe  Asn  Cys  Gly  Lys  Glu  Gly  His  Thr  Ala  Arg
                 50                      55                      60

AAU  UGC  AGG  GCC  CCU  AGG  AAA  AAG  GGC  UGU  UGG  AAA  UGU  GGA  AAG  GAA         239
Asn  Cys  Arg  Ala  Pro  Arg  Lys  Lys  Gly  Cys  Trp  Lys  Cys  Gly  Lys  Glu
       65                      70                      75

GGA  CAC  CAA  AUG  AAA  GAU  UGU  ACU  GAG  AGA  CAG  GCU  AAU  UUU  UUA  GGG         287
Gly  His  Gln  Met  Lys  Asp  Cys  Thr  Glu  Arg  Gln  Ala  Asn  Phe  Leu  Gly
 80                      85                      90                      95

AAG  AUC  UGG  CCU  UCC  UAC  AAG  GGA  AGG  CCA  GGG  AAU  UUU  CUU  CAG  AGC         335
Lys  Ile  Trp  Pro  Ser  Tyr  Lys  Gly  Arg  Pro  Gly  Asn  Phe  Leu  Gln  Ser
                     100                     105                     110

AGA  CCA  GAG  CCA  ACA  GCC  CCA  CCA  UUU  CUU  CAG  AGC  AGA  CCA  GAG  CCA         383
Arg  Pro  Glu  Pro  Thr  Ala  Pro  Pro  Phe  Leu  Gln  Ser  Arg  Pro  Glu  Pro
                     115                     120                     125

ACA  GCC  CCA  CCA  GAA  GAG  AGC  UUC  AGG  UCU  GGG  GUA  GAG  ACA  ACA  ACU         431
Thr  Ala  Pro  Pro  Glu  Glu  Ser  Phe  Arg  Ser  Gly  Val  Glu  Thr  Thr  Thr
                     130                     135                     140

CCC  CCU  CAG  AAG  CAG  GAG  CCG  AUA  GAC  AAG  GAA  CUG  UAU  CCU  UUA  ACU         479
```

| Pro | Pro | Gln | Lys | Gln | Glu | Pro | Ile | Asp | Lys | Glu | Leu | Tyr | Pro | Leu | Thr |
|---|---|---|---|---|---|---|---|---|---|---|---|---|---|---|---|
| | 145 | | | | 150 | | | | | 155 | | | | | |

UCC CUC AGA UCA CUC UUU GGC AAC GAC CCC UCG UCA CAA UAAAGAUAGG 528
Ser Leu Arg Ser Leu Phe Gly Asn Asp Pro Ser Ser Gln
160                      165                     170

GGGGCAACUA AAGGAAGCUC UAUUAGAUAC AGGAGCAGAU GAUACAGUAU UAGAAGAAAU 588

GAGUUUGCCA GGAAGAUGGA AACCAAAAAU GAUAGGGGGA AU 630

( 2 ) INFORMATION FOR SEQ ID NO:6:

( i ) SEQUENCE CHARACTERISTICS:
        ( A ) LENGTH: 172 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

Ala Thr Leu Glu Glu Met Met Thr Ala Cys Gln Gly Val Gly Gly Pro
 1           5                  10                  15

Gly His Lys Ala Arg Val Leu Ala Glu Ala Met Ser Gln Val Thr Asn
             20                  25                  30

Thr Ala Thr Ile Met Met Gln Arg Gly Asn Phe Arg Asn Gln Arg Lys
             35                  40                  45

Met Val Lys Cys Phe Asn Cys Gly Lys Glu Gly His Thr Ala Arg Asn
     50              55                  60

Cys Arg Ala Pro Arg Lys Lys Gly Cys Trp Lys Cys Gly Lys Glu Gly
 65              70                  75                      80

His Gln Met Lys Asp Cys Thr Glu Arg Gln Ala Asn Phe Leu Gly Lys
                 85                  90                  95

Ile Trp Pro Ser Tyr Lys Gly Arg Pro Gly Asn Phe Leu Gln Ser Arg
                 100                 105                 110

Pro Glu Pro Thr Ala Pro Pro Phe Leu Gln Ser Arg Pro Glu Pro Thr
             115                 120                 125

Ala Pro Pro Glu Glu Ser Phe Arg Ser Gly Val Glu Thr Thr Thr Pro
     130             135                 140

Pro Gln Lys Gln Glu Pro Ile Asp Lys Glu Leu Tyr Pro Leu Thr Ser
 145             150                 155                     160

Leu Arg Ser Leu Phe Gly Asn Asp Pro Ser Ser Gln
                 165                 170

( 2 ) INFORMATION FOR SEQ ID NO:7:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 3..17

( x i ) SEQUENCE DESCRIPTION: SEQ ID NO:7:

GC AGC ATC GCG ATG CCT A 18
   Ser Ile Ala Met Pro
    1               5

( 2 ) INFORMATION FOR SEQ ID NO:8:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: protein ( x i ) SEQUENCE DESCRIPTION: SEQ ID NO:8:

```
Ser  Ile  Ala  Met  Pro
 1               5
```

( 2 ) INFORMATION FOR SEQ ID NO:9:

( i ) SEQUENCE CHARACTERISTICS:
    ( A ) LENGTH: 10 amino acids
    ( B ) TYPE: amino acid
    ( D ) TOPOLOGY: linear ( i i ) MOLECULE TYPE: protein ( x i ) SEQUENCE DESCRIPTION: SEQ ID NO:9:

```
Val  Val  Gln  Gly  Glu  Glu  Phe  Ala  Val  Gly
 1               5                             10
```

( 2 ) INFORMATION FOR SEQ ID NO:10:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:10:

TGACGCTCTC GCACCCATCT CTCACCAGTC GCCGCCCTC    39

( 2 ) INFORMATION FOR SEQ ID NO:11:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:11:

CTCTCTCCTT CTAGCCTCCG CTCACCAGTC GCCGCCCCTC    40

( 2 ) INFORMATION FOR SEQ ID NO:12:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:12:

TGCCCTTCTT TGCCATAATT GAAATACTTA ACAATCTTTC    40

( 2 ) INFORMATION FOR SEQ ID NO:13:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:13:

TGTCCTTCCT TTCGATATTT CCAATAGCCC TTTTTCCTAG    40

-continued ( 2 ) INFORMATION FOR SEQ ID NO:14:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:14:

C C A T C G A T C T A A T T C T C 1 7

( 2 ) INFORMATION FOR SEQ ID NO:15:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( x i ) SEQUENCE DESCRIPTION: SEQ ID NO:15:

G G C C A G A T C T T C C C T A A 1 7

We claim:

1. A nucleic acid construct which encodes non-infectious HIV particles and, when expressed in mammalian cells, produces only non-infectious HIV particles having no genomic RNA, the construct having an alteration of the wild type HIV genome, the alteration selected from the group consisting of:

a) deletion in the ψ site, wherein the deletion is selected from the group consisting of:
   1) deletion of nucleotides 293 to 331, inclusive; and
   2) deletion of nucleotides 293 to 313, inclusive;
b) an alteration in the gag gene which results in an alteration of the amino acid sequence of the encoded protein, the amino acid alteration selected from the group consisting of:
   1) substitution of tyrosine for the first two cysteines of the 5' CysHis box;
   2) substitution of tyrosine for the first two cysteines of the 3' CysHis box;
   3) substitution of tyrosine for the first two cysteines of both CysHis boxes;
   4) deletion of both CysHis boxes and the amino acid sequence between them; and
   5) alteration of the length of the amino acid sequence between the two CysHis boxes; and
c) deletion in the ψ site and an alteration in the gag gene which results in an alteration of the amino acid sequence of the encoded protein, wherein:
   1) the deletion in the ψ site is selected from the group consisting of:
      a) deletion of nucleotides 293 to 331, inclusive; and
      b) deletion of nucleotides 293 to 313, inclusive; and
   2) the alteration in the gag gene is selected from the group consisting of:
      a) substitution of tyrosine for the first two cysteines of the 5' CysHis box;
      b) substitution of tyrosine for the first two cysteines of the 3' CysHis box;
      c) substitution of tyrosine for the first two cysteines of both CysHis boxes;
      d) deletion of both CysHis boxes and the amino acid sequence between them; and
      e) alteration of the length of the amino acid sequence between the two CysHis boxes.

2. The construct of claim 1, which is selected from the group consisting of pA3HXB and pA4HXB.

3. The nucleic acid construct of claim 1, which is selected from the group consisting of:

a) pA15HXB;
b) pA14HXB;
c) pA14-15HXB; and
d) PΔCH1-2HXB.

4. The nucleic acid construct of claim 1, which is selected from the group consisting of pΔPAC1 and pΔPAC-Hygro.

5. The nucleic acid construct of claim 1, further comprising an alteration selected from the group consisting of:

a) an alteration which results in substitution of the envelope precursor cleavage site with VVQGEEFAVG (SEQ ID NO:9);
b) deletion of the primer binding site; and
c) a combination of 1) an alteration which results in substitution of the envelope precursor cleavage site with VVOGEEFAVG and 2) deletion of the primer binding site.

6. The construct of claim 5, which is selected from the group consisting of pΔPAC2 and pΔPAC3.

7. The nucleic acid construct of claim 1, further comprising an SV40 origin of replication.

8. The nucleic acid construct of claim 1, wherein the alteration of the wildtype genome further comprises a selectable marker gene in place of the nef gene.

9. The nucleic acid construct of claim 8, wherein said selectable marker gene encodes a selectable marker which is selected from the group consisting of: neomycin resistance, hygromycin resistance and dihydrofolate reductase.

10. The nucleic acid construct of claim 1 further comprising the HIV-1 genome in which the nef gene is replaced by a selectable marker gene, the nucleic acid construct encoding non-infectious mutant HIV particles which contain essentially the same major structural proteins as wildtype HIV-1 and lack the HIV-1 genome.

11. The nucleic acid construct of claim 10, wherein the selectable marker gene encodes a selectable marker which is selected from the group of consisting of neomycin resistance, hygromycin resistance, genes and dihydrofolate reductase.

12. The construct of claim 1, further comprising an HIV env gene from another HIV strain or isolate which is substituted for a native HIV env gene of the construct.

13. A mammalian cell line, transfected with the construct of claim 1, which stably produces HIV packaging mutant virions, all of which are completely non-infectious.

14. The cell line of claim 13, wherein the construct is stably integrated in the genome of the cell line, and the cell line stably produces the completely non-infectious HIV particles.

15. A method for producing non-infectious HIV particles having no genomic RNA, comprising the steps of:
   a) transfecting a mammalian cell line with a nucleic acid construct which encodes non-infectious HIV particles, the construct having an alteration of the wild type HIV genome, the alteration selected from the group consisting of:
      1) deletion in the ψ site, wherein the deletion is selected from the group consisting of:
         a) deletion of nucleotides 293 to 331, inclusive; and
         b) deletion of nucleotides 293 to 313, inclusive;
      2) an alteration in the gag gene which results in an alteration of the amino acid sequence of the encoded protein, the amino acid alteration selected from the group consisting of:
         a) substitution of tyrosine for the first two cysteines of the 5' CysHis box;
         b) substitution of tyrosine for the first two cysteines of the 3' CysHis box;
         c) substitution of tyrosine for the first two cysteines of both CysHis boxes;
         d) deletion of both CysHis boxes and the amino acid sequence between them;
         e) alteration of the length of the amino acid sequence between the two CysHis boxes; and
      3) a deletion in the ψ site and an alteration in the gag gene which results in an alteration of the amino acid sequence of the encoded protein, wherein:
         a) the deletion in the ψ site is selected from the group consisting of:
            1) deletion of nucleotides 293 to 331, inclusive; and
            2) deletion of nucleotides 293 to 313, inclusive; and
         b) the alteration in the gag gene is selected from the group consisting of:
            1) substitution of tyrosine for the first two cysteines of the 5' CysHis box;
            2) substitution of tyrosine for the first two cysteines of the 3' CysHis box;
            3) substitution of tyrosine for the first two cysteines of both CysHis boxes;
            4) deletion of both CysHis boxes and the amino acid sequence between them; and
            5) alteration of the length of the amino acid sequence between the two CysHis boxes; and
   b) expressing the construct in the cell line, thereby producing only completely non-infectious HIV particles.

16. Non-infectious HIV particles which are produced by the method of claim 15, wherein said particles contain the HIV gag, env and reverse transcriptase proteins and lack the HIV genomic RNA.

17. Non-infectious HIV virions which are produced by growing a mammalian cell line transfected with the construct of claim 1 under conditions appropriate for production of the completely non-infectious HIV particles.

18. A mammalian cell line, transfected with the nucleic acid construct of claim 5, which produces only mutant HIV particles which are non-infectious.

19. The cell line of claim 18, wherein the nucleic acid construct is stably integrated in the genome of the cell line, and the cell line stably produces the non-infectious HIV particles.

20. A mammalian cell line transfected with a nucleic acid construct which encodes completely non-infectious HIV particles having no genomic RNA, the construct selected from the group consisting of:
   a) pA3HXB;
   b) pA4HXB;
   c) pA14HXB;
   d) pA15HXB;
   e) pA14-15HXB;
   f) pΔCH1-2HXB;
   g) pΔPAC1;
   h) pΔPAC-Hygro;
   i) pΔPAC2; and
   j) pΔPAC3,
wherein the cell line produces the completely non-infectious HIV particles.

21. The cell line of claim 20, wherein the construct is stably integrated in the genome of the cell line and the cell line produces the non-infectious HIV mutant virion encoded by the nucleic acid construct.

22. A mammalian cell line transfected with the construct of claim 12 and producing completely non-infectious HIV particles.

23. The cell line of claim 22, wherein the construct is stably integrated in the genome of the cell line, and the cell line stably produces the completely non-infectious HIV particles.

24. A method of producing non-infectious HIV particles having no genomic RNA, comprising growing a mammalian cell line transfected with a nucleic acid construct selected from the group of:
   a) pA3HXB;
   b) pA4HXB;
   c) pA14HXB;
   d) pA15HXB;
   e) pA14-15HXB;
   f) pΔCH1-2HXB;
   g) pΔPAC1;
   h) pΔPAC-Hygro;
   i) pΔPAC2; and
   j) pΔPAC3,
under conditions suitable for expression of the nucleic acid construct, whereby non-infectious HIV particles are produced.

25. Non-infectious HIV particles which are produced by the method of claim 24, wherein said particles contain the HIV gag, env and reverse transcriptase proteins and lack the HIV genomic RNA.

26. The method of claim 15, wherein the construct further comprises an alteration selected from the group consisting of:
   a) substitution of a selectable marker in place of the nef gene;
   b) substitution of an HIV env gene from another HIV strain or isolate in place of the native env gene of the construct; and
   c) substitution of a selectable marker in place of the nef gene and substitution of an HIV env gene from another HIV strain or isolate in place of the native env gene of the construct.

* * * * *

UNITED STATES PATENT AND TRADEMARK OFFICE
CERTIFICATE OF CORRECTION

PATENT NO. : 5,861,282
DATED : January 19, 1999
INVENTOR(S) : Anna Aldovini, Richard A. Young, Mark B. Feinberg, Didier Trono and David Baltimore It is certified that error appears in the above-identified patent and that said Letters Patent is hereby corrected as shown below:

In column 26, line 42, Claim 5, please delete "VVOGEEFAVG" and replace it with --VVQGEEFAVG--.

In column 27, line 9, Claim 15, please delete "having no genomic RNA".

In column 27, line 11, Claim 15, after "HIV particles" but before the comma, please add --having no genomic RNA--.

Signed and Sealed this

Twelfth Day of October, 1999

Attest:

Q. TODD DICKINSON

Attesting Officer

Acting Commissioner of Patents and Trademarks